(12) United States Patent
Yodfat et al.

(10) Patent No.: US 8,696,570 B2
(45) Date of Patent: Apr. 15, 2014

(54) INSERTION DEVICE AND METHOD FOR INSERTING A SUBCUTANEOUSLY INSERTABLE ELEMENT INTO BODY

(75) Inventors: Ofer Yodfat, Maccabim-Reut (IL); Gavriel J. Iddan, Haifa (IL); Avraham Neta, Gilon (IL); Ruthy Kaidar, Haifa (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 11/989,684

(22) PCT Filed: Nov. 26, 2007

(86) PCT No.: PCT/IL2007/001454
§ 371 (c)(1),
(2), (4) Date: Apr. 26, 2010

(87) PCT Pub. No.: WO2008/065646
PCT Pub. Date: Jun. 5, 2008

(65) Prior Publication Data
US 2010/0217105 A1     Aug. 26, 2010

Related U.S. Application Data

(60) Provisional application No. 60/861,345, filed on Nov. 28, 2006.

(51) Int. Cl.
*A61B 5/145* (2006.01)
*A61M 5/00* (2006.01)

(52) U.S. Cl.
USPC ........ 600/365; 600/309; 600/347; 604/93.01; 604/164.01; 604/164.09

(58) Field of Classification Search
USPC .................. 600/309, 369, 365, 316, 345, 347; 604/48, 164.01, 187
See application file for complete search history.

(56) References Cited

U.S. PATENT DOCUMENTS

| 4,755,173 A | 7/1988 | Konopka et al. |
| 5,176,662 A | 1/1993 | Bartholomew et al. |

(Continued)

FOREIGN PATENT DOCUMENTS

| GB | 2 414 398 A | 11/2005 |
| WO | WO 03/090509 A | 11/2003 |

(Continued)

OTHER PUBLICATIONS

International Search Report, PCT Application No. PCT/IL2007/001454 dated Apr. 25, 2008.

(Continued)

*Primary Examiner* — Navin Natnithithadha
*Assistant Examiner* — Meredith Weare
(74) *Attorney, Agent, or Firm* — Mintz, Levin, Cohn, Ferris, Glovsky and Popeo, P.C.

(57) ABSTRACT

An insertion device for a fluid delivery device for delivering a therapeutic fluid to a body of a patient and/or for sensing of a bodily analyte is disclosed. The insertion device includes a housing and accommodated therein at least one penetrating cartridge provided with a penetrating member and with a subcutaneously insertable element; The insertion device is provided with a displacement mechanism which upon actuation is capable of protracting the penetrating cartridge towards the said device for delivery and/or sensing, wherein said protracting results in inserting of the penetrating cartridge into subcutaneous compartment of the body via an opening provided at the said device for delivery and/or sensing and said insertion device allows evacuation of the penetrating member from the subcutaneous compartment via the said opening.

35 Claims, 20 Drawing Sheets

(56) References Cited

U.S. PATENT DOCUMENTS

| | | | |
|---|---|---|---|
| 5,257,980 A | | 11/1993 | Van Antwerp et al. |
| 5,390,671 A | | 2/1995 | Lord et al. |
| 5,540,664 A | * | 7/1996 | Wyrick .................. 604/136 |
| 5,568,806 A | | 10/1996 | Cheney, II et al. |
| 5,586,553 A | | 12/1996 | Halili et al. |
| 5,611,806 A | * | 3/1997 | Jang .................. 606/167 |
| 5,820,622 A | * | 10/1998 | Gross et al. .................. 604/890.1 |
| 6,093,172 A | * | 7/2000 | Funderburk et al. .......... 604/135 |
| 6,699,218 B2 | | 3/2004 | Flaherty et al. |
| 6,830,562 B2 | | 12/2004 | Mogensen et al. |
| 2004/0133164 A1 | | 7/2004 | Funderburk |
| 2004/0158207 A1 | * | 8/2004 | Hunn et al. .............. 604/164.01 |
| 2004/0162521 A1 | | 8/2004 | Bengtsson |
| 2005/0101912 A1 | | 5/2005 | Faust et al. |
| 2006/0036139 A1 | * | 2/2006 | Brister et al. .................. 600/345 |
| 2006/0263839 A1 | * | 11/2006 | Ward et al. ...................... 435/14 |
| 2007/0027430 A1 | * | 2/2007 | Hommann .................. 604/207 |
| 2007/0106218 A1 | | 5/2007 | Yodfat et al. |
| 2010/0217230 A1 | | 8/2010 | Yodfat et al. |

FOREIGN PATENT DOCUMENTS

| | | | | | |
|---|---|---|---|---|---|
| WO | WO 2004/024211 A2 | | 3/2004 | | |
| WO | WO 2005058396 A1 | * | 6/2005 | ............. | A61M 5/20 |
| WO | WO 2005/065748 A1 | | 7/2005 | | |
| WO | WO 2005/112800 | * | 12/2005 | ............. | A61B 17/34 |
| WO | WO 2005/112800 A | | 12/2005 | | |
| WO | WO 2006/015600 A | | 2/2006 | | |
| WO | WO 2006/061354 | | 6/2006 | | |

OTHER PUBLICATIONS

Written Opinion and International Search Report for PCT Application No. PCT/IL2007/001454, mailed Apr. 25, 2008.

\* cited by examiner

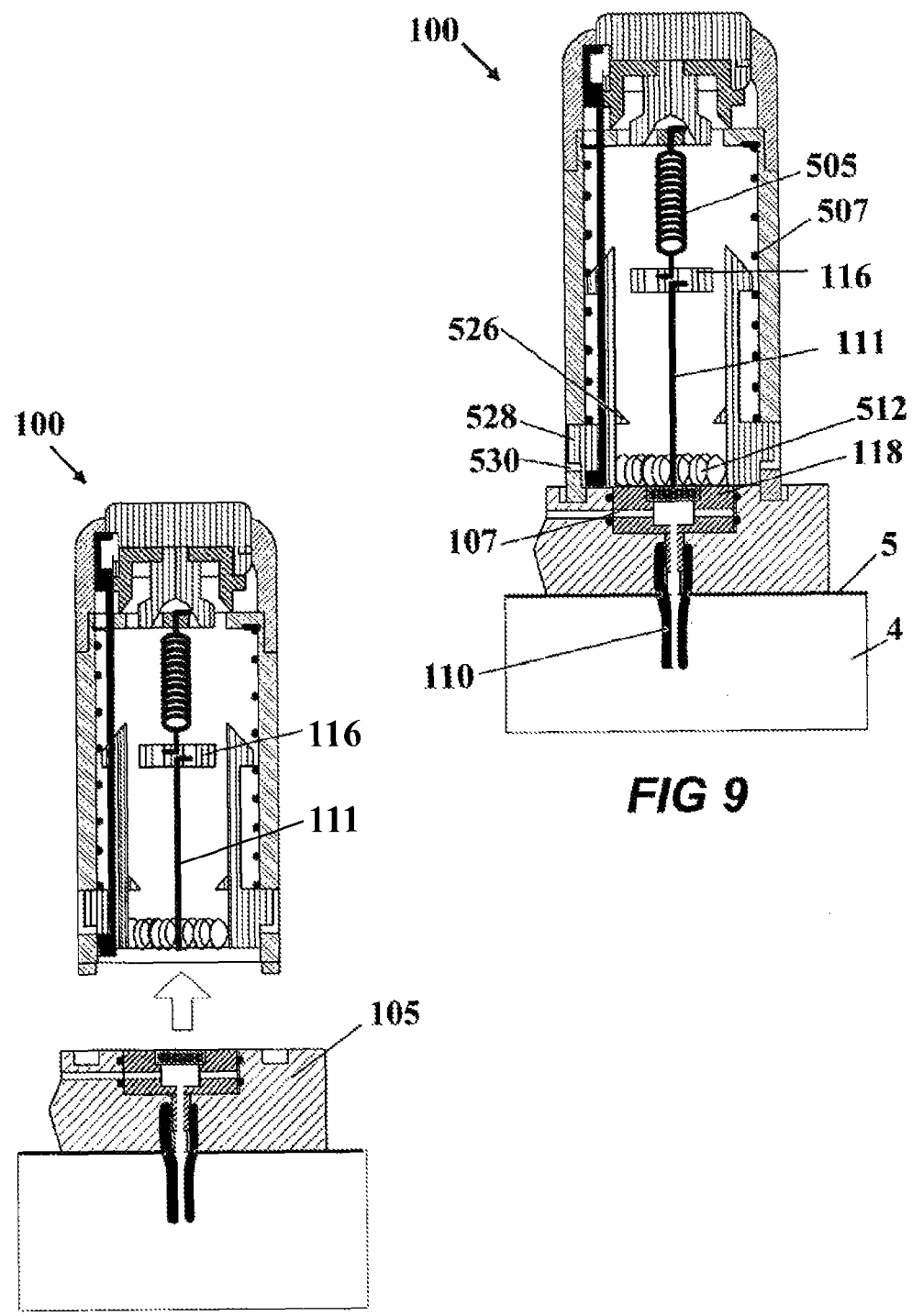

INSERTION DEVICE AND METHOD FOR INSERTING A SUBCUTANEOUSLY INSERTABLE ELEMENT INTO BODY

CROSS REFERENCE TO RELATED APPLICATIONS

This application is a National Stage entry of PCT/IL07/001454, having an International filing date of Nov. 26, 2007, which claims priority to U.S. provisional patent application No. 60/861,345, filed Nov. 28, 2006. Each of the foregoing disclosures is expressly incorporated herein in its entirety.

FIELD OF THE INVENTION

This invention relates to medical devices, and more particularly to a device, which assists in insertion of a cannula, which is suitable for subcutaneous administering of a medication into the skin of a patient and/or for sensing analyte levels in a body fluid. Even more particularly, the present invention is directed to an insertion device for manual or automatic insertion of a cannula for delivery of a drug supplied by an infusion pump and/or for continuous sensing of a subcutaneous body analyte.

BACKGROUND OF THE INVENTION

Continuous subcutaneous delivery of medication or monitoring of a body analyte is often accomplished through the use of a cannula, which should remain in place for several days. Diabetes patients may use such a cannula as a subcutaneous compartment for continuous delivery of insulin by pumps or for monitoring interstitial glucose levels by sensors. A combination of a tube, connecting the insulin pump to the cannula and a detachable connector is often referred to as an infusion set. Such infusion sets and modes of their insertion are disclosed, for example, in U.S. Pat. Nos. 4,755,173, 5,176,662 and 5,257,980. Subcutaneous cannula insertion modes for continuous glucose monitoring are disclosed for example in U.S. Pat. Nos. 5,390,671, 5,568,806 and 5,586,553. Usually transcutaneous cannula insertion can be carried out with a sharp metal penetrating member to be withdrawn after skin pricking. This procedure can be effected manually by the patient. The insertion is usually painful and requires considerable skill. Some patients are reluctant or hesitant to pierce their own skin, and thus encounter difficulties in proper cannula insertion. Such difficulties can be attributable to insufficient manual dexterity or alternately to anxiety associated with anticipated discomfort as the needle pierces the skin. This problem can be especially significant when an insulin pump is used since misplacement of the cannula can cause kinking, incorrect insertion angle or incorrect cannula insertion depth leading eventually to cannula obstruction. As a result of this, delivery of insulin may be life threatening.

In an attempt to cope with this problem, automatic infusion set inserters were developed to assure the correct placement of the cannula in the subcutaneous layer, at the correct angle, while minimizing pain and hazardous obstructions associated with cannula insertion. U.S. Pat. Nos. 6,093,172 and 6,830,562 disclose injector devices comprising a spring-loaded plunger for an automatic subcutaneous placement of an infusion set. An automatic cannula insertion is also employed in the skin adhered insulin pump disclosed in U.S. Pat. No. 6,699,218 assigned to Flaherty et al. Unfortunately, this device is relatively bulky, heavy and indiscreet because the spring loaded mechanism is enclosed within the housing during the entire period of usage.

A skin adherable insulin delivery device was disclosed in co-owned U.S. Provisional Patent Application No. 60/837,877. This device includes a unique apparatus for cannula insertion, which does not require an infusion set and long tubing. The cannula insertion apparatus allows the patient to choose the desired depth for cannula insertion and the desired insertion angle. The device is provided with a "well-assembly" connected to the insulin delivery tube. The well assembly has an upper opening and a lower rubber gasket. The insertion apparatus is provided also with a "penetrating cartridge" having a cannula, a penetrating member and a rubber cap. The penetrating cartridge allows for the cannula to penetrate through the well assembly and then through skin, while sealing the upper opening and maintaining the delivery of insulin.

Thus, despite existence of several solutions for cannula insertion, there still exists a need for a device that facilitates cannula insertion within the subcutaneous layer. In particular there is a need for a device for inserting a cannula, which would be suitable for inserting a cannula for delivery of a medication to a patient, by a patch type fluid delivery pump.

There is also a need for a device, which facilitates insertion of a cannula, which would be suitable for continuous analyte monitoring (i.e. continuous glucose monitor).

There is also a need for a device that inserts a cannula at any desired angle.

There is also a need for a device that allows insertion of a cannula at any desired depth.

There is also a need for a cannula insertion device that maintains precise alignment of the cannula relative to the well-assembly. Highly accurate alignment is important for the following reasons:
  1. To avoid tearing of the well's lower gasket, thus maintaining intact sealing;
  2. To permit skin penetration at a desired angle;
  3. To seal of the upper opening with the rubber cap; and
  4. For precise placement of the cannula within the well and maintaining flow communication.

There is also a need for a cannula inserter that can be precisely aligned with the well and subsequently allows pivoting of the well to a desired penetration angle. The inserter itself may serve as a rotating handle which increases the moment applied to the well, thus preventing direct contact between the user's hands and the delicate, sterile, miniature well.

There is also a need for a device that allows manual cannula insertion.

There is also a need for a device that allows automatic cannula insertion.

There is also a need for a cannula insertion device that can be loaded with more than one cannula and thus allows multiple insertions.

In the current disclosure, the device for cannula insertion will be referred to as a cannula inserter or simply as an inserter. In addition, in the current disclosure, the patch type fluid delivery pump will be referred to as the patch.

SUMMARY OF THE INVENTION

Some of the embodiments of the present invention are directed to an inserter for precise placement of a subcutaneously insertable element, i.e. a cannula or a sensor within a user's subcutaneous tissue. The device is intended for automatic or manual insertion of the insertable element through a fluid delivery pump. The pump may be a patch type pump adherable to the user's body and suitable for controllable fluid delivery or continuous analyte level monitoring. Despite in the further description delivering of the therapeutic fluid via a cannula will be mentioned, this should not be understood as limiting the present invention to inserting of merely a cannula. The present invention refers equally to an insertion device capable of inserting any other subcutaneously insertable elements, e.g. a sensor for sensing of a bodily analyte.

In some embodiments, the delivered fluid is insulin and the monitored analyte is glucose. The skin adhered patch pump contains a fluid reservoir, a well and a delivery tube through which the fluid is delivered from the reservoir to the well. The well includes an opening arranged within the patch pump housing. The well allows fluid dripping during priming (purging the air out of the reservoir and out of the delivery tube). The well also maintains fluid communication between the delivery tube and the user's body after cannula insertion. The well has an upper side opening and a self-sealing rubber septum on its lower side. The inserter allows automatic insertion of a penetrating cartridge into the tissue and either manual or automatic retraction of the penetrating member from the tissue. The penetrating cartridge has a subcutaneously insertable element, a penetrating member provided with a grip portion and a well sealing cap. The penetrating cartridge is contained within the inserter and is fired by a spring loaded mechanism, activated by the user. During insertion, the penetrating member and the subcutaneously insertable element pierce the septum at the well's lower side and then pierce the skin, and penetrate the subcutaneous region. Concomitantly, the well sealing cap seals the opening at the well's upper side. After completing the insertion, the penetrating member is retracted back outside of the skin and outside the well, either manually or automatically.

In one embodiment of the invention it concerns an insertion device for use in a device for delivery of a therapeutic fluid to a body of a patient and/or for sensing an analyte. The insertion device is provided with a housing loadable by at least one penetrating cartridge consisting of a subcutaneously insertable element and a penetrating member for penetrating the subcutaneous tissue and delivering the subcutaneously insertable element to the subcutaneous tissue. The housing also includes a trigger coupled to the penetrating cartridge to actuate insertion of the penetrating member along with the subcutaneously insertable element into the subcutaneous tissue, while the insertion takes place via the device for delivery of the therapeutic fluid and/or for sensing a bodily analyte. The insertion can take place only when the penetrating cartridge is located at a predetermined position with respect to the subcutaneous tissue. In an embodiment the insertion device is provided with a safety means, which prevents accidental insertion of the penetrating member and the subcutaneously insertable member. In still further embodiment the insertion device is provided with a retracting mechanism enabling automatic retraction of the penetrating member from the subcutaneous tissue. In still further embodiment the subcutaneously insertable element is a cannula for delivering a therapeutic fluid. In yet another embodiment the subcutaneously insertable element is a sensor for sensing a bodily analyte.

In another embodiment of the invention, a method for delivering therapeutic fluid to a body of a patient and/or for sensing of a bodily analyte is provided. The method includes providing a device for delivering of a therapeutic fluid to a body of a patient and/or for sensing of a bodily analyte, while said device being provided with an insertion device according to the above noted embodiment. The insertion device is loadable by at least one penetrating cartridge having a subcutaneously insertable element and a penetrating member. The method further comprises inserting the penetrating member and the subcutaneously insertable element into the subcutaneous tissue, removing the penetrating member from the tissue, while allowing the subcutaneously insertable element to remain in the subcutaneous tissue. The method further comprises delivering therapeutic fluid to the body of the patient and/or sensing of bodily analyte through the subcutaneously insertable element.

In another embodiment of the invention, the insertion device is provided with a spring loaded actuator for initiation of insertion the penetrating member and the subcutaneously insertable element to the subcutaneous tissue and removal of the penetrating member from the subcutaneous tissue after the subcutaneously insertable element is inserted into the subcutaneous tissue.

In yet another embodiment of the invention, the insertion device comprises a safety means for enabling insertion of the penetrating member only when the insertion device is placed in a predetermined position with respect to the, device for delivery and/or for sensing where the safety means includes a safety rod configured to be positioned at a predetermined location to enable discharge of the penetrating member, a trigger for initiating discharge of the penetrating member into the subcutaneous tissue and a retractor for retracting the penetrating member after insertion and for retaining the cannula inside the subcutaneous tissue, where the retracting of the penetrating member is configured to be automatic.

In yet another embodiment of the invention, a method for inserting a subcutaneously insertable element within a subcutaneous tissue of a patient using an insertion device according to any of the preceding embodiments is provided, where the method includes inserting the penetrating member and the subcutaneously insertable element into the body and removing the penetrating member by gripping the grip portion thereof while retaining the subcutaneously insertable element in the body and further retaining the well sealing cap at an upper opening of the well.

Thus, it is an object of some of the embodiments of the present invention to provide a new insertion device and a method for automatic insertion of a cannula or a sensor into a user's body.

It is another object of some of the embodiments of the present invention to provide an reusable or disposable inserter that can employ automatically or manually retractable penetrating member. In one embodiment such disposable inserter is preloaded with a penetrating cartridge and after insertion the used penetrating member is retracted and remains within the inserter housing, which is then discarded together with the inserter.

In one reusable configuration of the inserter, the used penetrating member remains attached to the pump housing and should be manually removed therefrom.

It is another object of some of the embodiments of the present invention to provide a device for automatic cannula or sensor insertion, which is intended for use in association with a skin adherable pump.

It is another object of some of the embodiments of the present invention to provide an inserter that is adapted to insert a cannula or a sensor through a well assembly.

It is another object of some of the embodiments of the present invention to provide an inserter that allows the insertion of a penetrating cartridge through a well and then through the skin. After insertion, the cannula or sensor brought in the tissue remains in the body, the well sealing cap seals the opening at the well's upper side and the penetrating member is retracted while being gripped at a grip portion.

It is another object of some of the embodiments of the present invention to provide an inserter that enables alignment of the cannula or sensor with the patch housing and with the well.

It is another object of some of the embodiments of the present invention to provide an inserter that allows cannula or sensor insertion at any desired penetration angle.

It is another object of some of the embodiments of the present invention to provide an inserter that allows automatic insertion of the penetrating member and automatic retraction of the penetrating member.

It is another object of some of the embodiments of the present invention to provide an inserter that allows automatic insertion of the penetrating member and manual retraction of the penetrating member.

It is another object of some of the embodiments of the present invention to provide an inserter that can be preloaded with at least one penetrating cartridge.

It is another object of some of the embodiments of the present invention to provide an inserter loadable by a penetrating cartridge.

It is another object of some of the embodiments of the present invention to provide an inserter that is provided with a cartridge drum suitable for retaining a plurality of the penetrating cartridges.

It is another object of some of the embodiments of the present invention to provide an inserter that contains a safety means for preventing inadvertent or premature insertion. The safety means could be integrated within the inserter or may be an additional component that is attachable to the inserter, and detachable before operation.

It is another object of some of the embodiments of the present invention to provide a safety means for guarding the sharp penetrating member after retraction thereof from the tissue.

BRIEF DESCRIPTION OF THE DRAWINGS

FIG. 9 illustrates an exemplary automatic insertion and retraction mechanism during automatic retraction, according to some embodiments of the present invention.

FIG. 10 illustrates an exemplary automatic insertion and retraction mechanism when insertion is completed, according to some embodiments of the present invention.

DETAILED DESCRIPTION OF THE INVENTION

The further description of the invention deals mostly with insertion of a cannula. It should be borne in mind however that this description may be equally used for insertion of a sensor for sensing bodily analyte or any other subcutaneously insertable element.

In some embodiments, the inserter is intended to insert a cannula into the user's body, for the purposes of delivering fluids. The cannula, which can be made from a soft material, can penetrate the skin by means of a penetrating member (a guide needle) which is retracted after insertion. A fluid delivery device, for example configured as a patch, adherable to the user's body, contains the fluid to be delivered. The cannula is inserted in the subcutaneous compartment of a body of a patient through a designated location on the patch, i.e. through a "well". The inserter, which is provided with a trigger, is placed on the patch above the well. After the trigger is fired the cannula and the penetrating member protracts and penetrates through the well into the skin, the penetrating member is then retracted from the subcutaneous compartment while the cannula remains thereinto and thus fluid communication is allowed between the fluid reservoir and the user's body via the cannula.

In some embodiments, the inserter includes the following features:
- A Position Enabling feature—a safety mechanism that allows firing only when the inserter has been placed in the appropriate position. In some embodiments, this safety means is provided with a safety rod, which has to be positioned properly to enable firing.
- An Accidental Firing Prevention Mechanism—a mechanism that mechanically prevents inadvertent firing. In some embodiments, the user has to operate the accidental firing prevention mechanism by turning and/or pulling a dedicated part provided in the inserter to enable firing.
- A Firing Trigger Mechanism—a mechanism that actuates the insertion operation.
- A Retraction Mechanism—a mechanism that pulls the penetrating member (guide needle) and retracts it from the body after insertion, while leaving the cannula inside the body. In some embodiments, the retraction of the penetrating member is carried out automatically, while in other embodiments the retraction is carried out manually by the patient.

Figure 1:
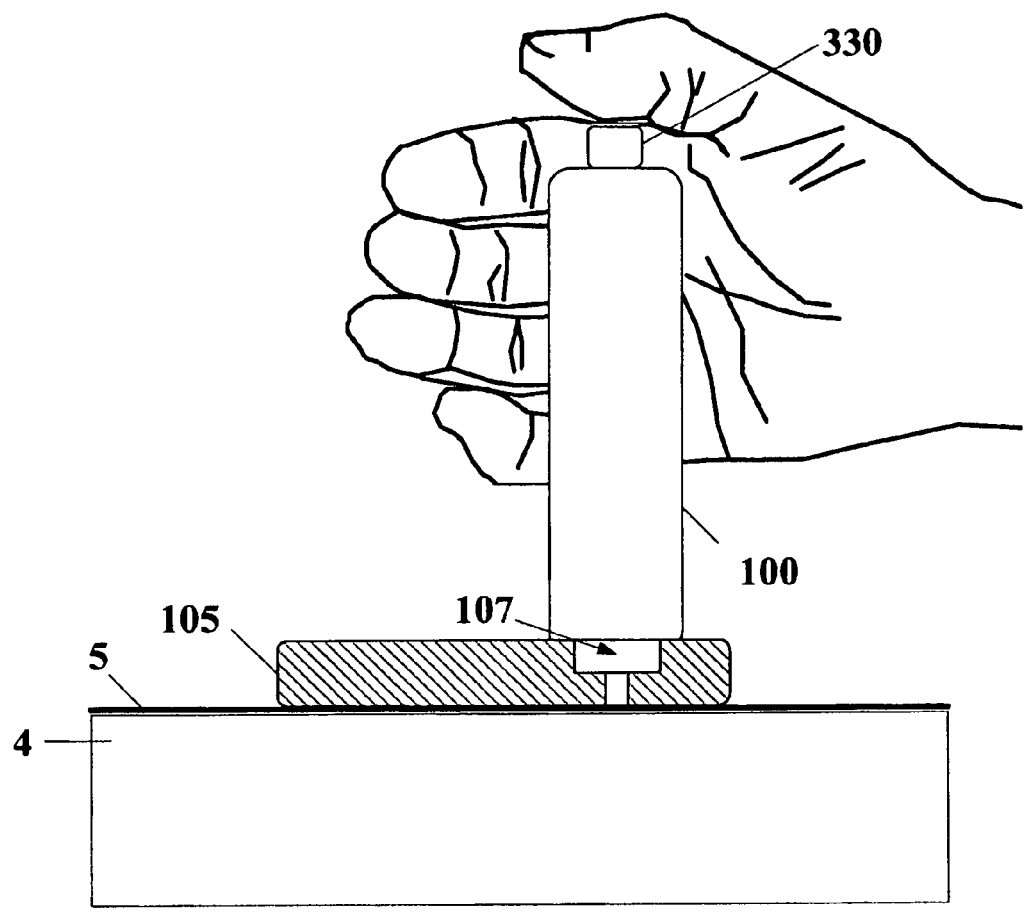
FIG. 1 is a general view of an exemplary inserter, according to some embodiments of the present invention.

FIG. 1 shows a general view of one of the embodiments of the present invention. An inserter (100) is ready to perform the insertion of a cannula along with a penetrating member into the user's body (4). The cannula is inserted through a well (107) that is provided at a patch type delivery pump (105). The patch is adherable to a patient's skin (5). The inserter (100) is operated by a trigger button (330), which is activated by the patient. In some embodiments (for example, as shown in FIG. 1), insertion can be accomplished when the inserter is deployed substantially perpendicular to the skin. This will be referred to as a perpendicular mode (90° penetration angle and/or thereabout). It should be understood however, that the penetration can be possible not only when the inserter is directed perpendicularly to the skin, but at any desired angle, which can be achieved using a pivoting well. An example of such pivoting well is disclosed in a co-owned U.S. Provisional Patent Application No. 60/837,877

The inserter can be gripped by hand and pivoted together with the well such that desired penetration angle can be chosen and cannula insertion can be carried out at that chosen penetration angle.

Figure 2:
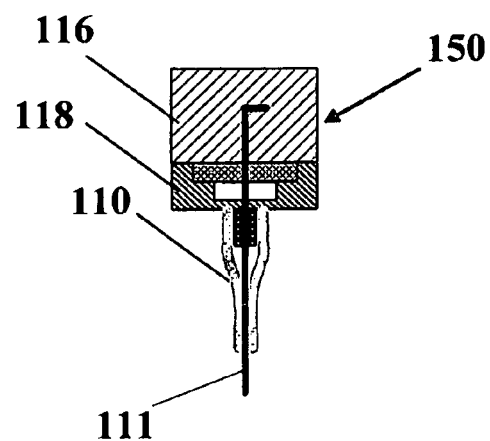
FIG. 2 illustrates an exemplary penetrating cartridge, according to some embodiments of the present invention.

In some embodiments, the inserter includes a penetrating cartridge, which is fired by the inserter into the skin. Such a penetrating cartridge is shown in FIG. 2 and includes the following parts:
- A penetrating member for puncturing the skin and allowing initial penetration to the user's body. The penetrating member may be configured as a needle provided with a sharp end, suitable for penetrating the skin.
- A grip portion located at the opposite, blunt end of the penetrating member. The grip portion is designed to be conveniently grasped by the patient. The grip portion may be grasped when the penetrating member is inserted into the body or when it is retracted therefrom.
- A soft cannula, which is insertable into the body along with the penetrating member. The cannula stays in the body, after the penetrating member has been removed from the body.
- A well sealing cap, which can be attached to the cannula. This cap is made of a self sealable rubber (e.g. Silicone rubber, Chlorobutyl rubber). After insertion, the cap seals the opening at the well's upper side, and thus prevents fluid leakage. The cap maintains sealing after retraction of the penetrating member.

In some embodiments, the insertion process is associated with the following steps:
- The penetrating cartridge, which includes penetrating member and cannula is subcutaneously inserted into the body.
- The penetrating member is removed from the body being gripped by its grip portion.
- The cannula remains in the body.
- The well sealing cap remains in the well and seals upper opening of the well.

FIG. 2 shows the penetrating cartridge (150) according to some embodiments, which comprises a penetrating member (111), having a sharp end and an opposite blunt end. The penetrating member is connected by its blunt end to a grip portion (116) of the cartridge. The cartridge can also include a cannula (110) surrounding the penetrating member and a well sealing cap (118) situated between the cannula and the grip portion.

Figure 3:
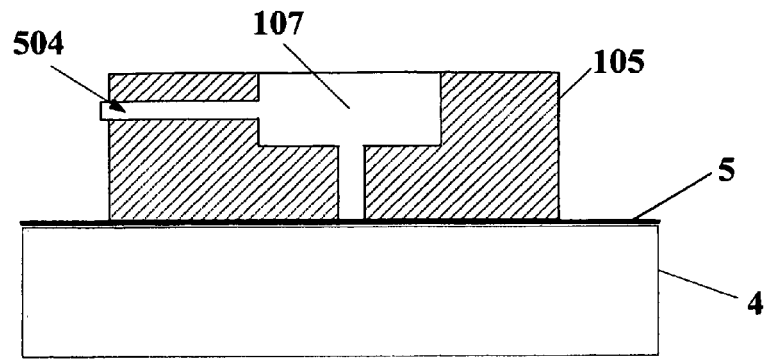
FIG. 3 illustrates an exemplary patch infusion pump, according to some embodiments of the present invention.

FIG. 3 illustrates an exemplary embodiment of the "well" (107) provided within the patch (105). The well is used to provide fluid communication between a delivery tube (504) and the cannula, which after insertion remains in the subcutaneous tissue (4) under the skin (5). The delivery tube (504) connects the fluid reservoir (not shown) and the well. During insertion, the needle (not shown in FIG. 3) passes through the well (107), before it penetrates the skin (5). The well (107) allows fluid delivery to the body from the reservoir through the delivery tube and through cannula.

Figure 4A:
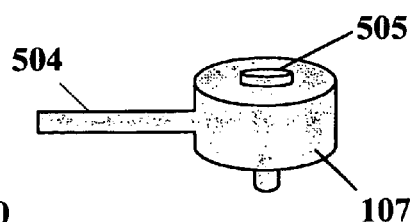
FIGS. 4a-c illustrate an exemplary well-arrangement, according to some embodiments of the present invention.
Figure 4B:
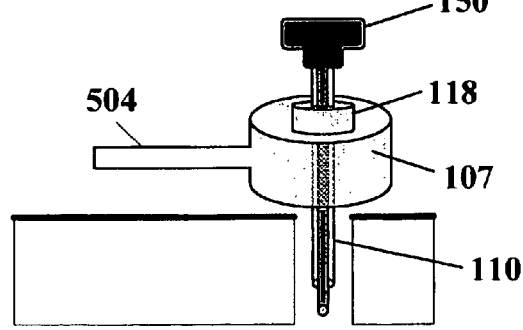
Figure 4C:
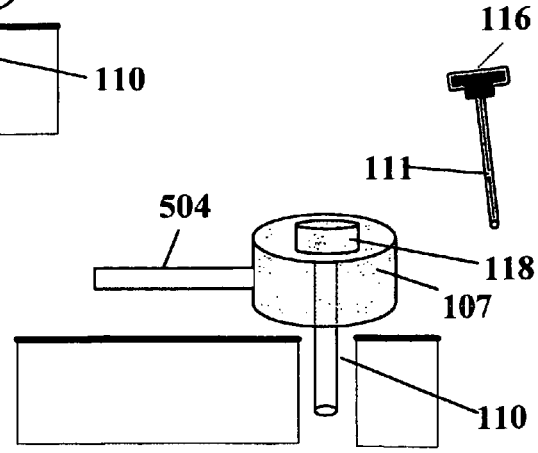

FIGS. 4a-c illustrate an exemplary embodiment of the basic principle of the cannula insertion through the well (107). This process can be carried out manually, semi-automatically (the insertion is carried out by the inserter while the patient manually retracts the penetrating member) or automatically (the insertion is carried out by the inserter and the penetrating member is retracted by the inserter).

FIG. 4a illustrates the well (107) having an opening (505) on its upper side and a self sealing rubber on its lower side. The opening allows fluid dripping during priming. FIG. 4b illustrates a situation in which the penetrating cartridge (150) is inserted into the well (107): the penetrating member and the cannula pierce the rubber septum at the well's lower side and then pierce the skin. Concomitantly, the well-sealing cap (118) closes the opening (505) at the well's upper side.

FIG. 4c illustrates the cannula after insertion and also after the penetrating member (111) has been retracted. The well (107) also has an inlet port on its circumference allowing a passage of dispensed fluid from the delivery tube (504) to the cannula (110), through a lateral opening made in the cannula (not shown in FIGS. 4a-c).

An exemplary embodiment of the well arrangement is disclosed in a co-owned/co-pending U.S. patent application Ser. No. 11/397,115. An exemplary embodiment of the penetrating cartridge is disclosed in a co-owned/co-pending U.S. Provisional Patent Application No. 60/837,887. The disclosures of the above application are incorporated herein by reference in their entireties.

Inserter for Automatic Insertion with Auto-retraction

In some embodiments, the inserter includes an automatic insertion and automatic retracting mechanism. In this embodiment, the patient first disables all safety mechanisms and then fires the trigger. The firing of the trigger causes an automatic insertion of the penetrating cartridge followed by automatic retraction of the penetrating member.

Figure 5:
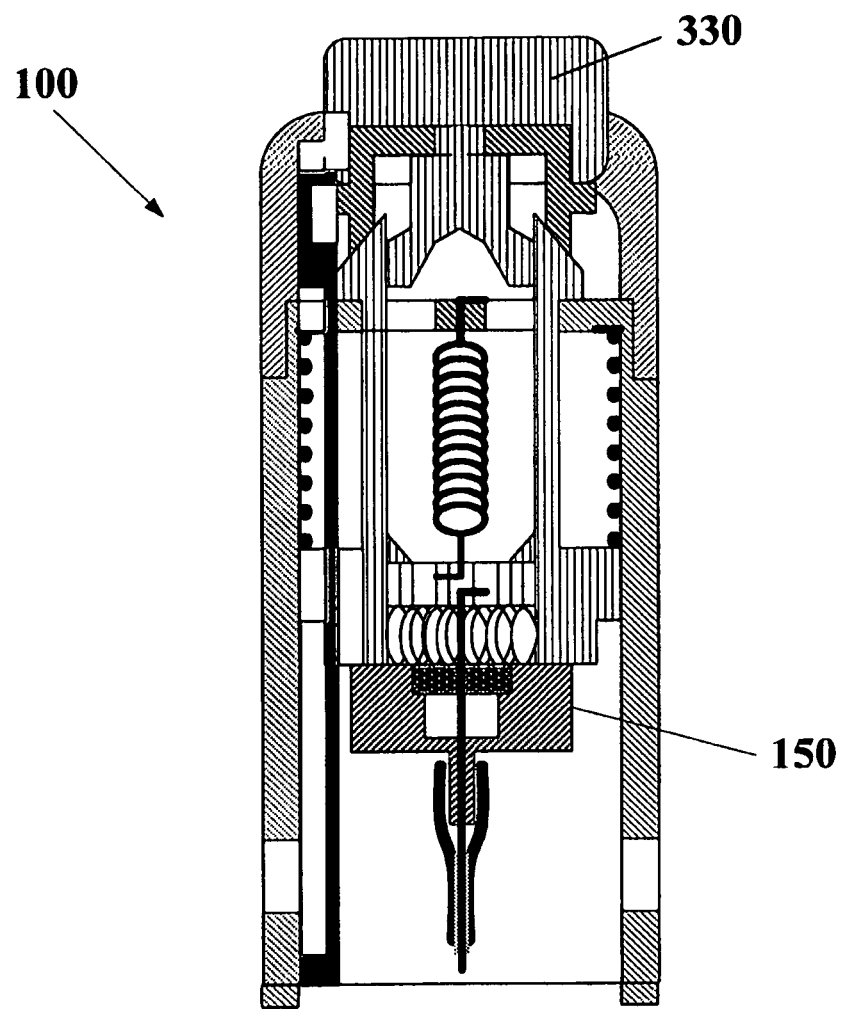
FIG. 5 illustrates an exemplary automatic insertion and retraction mechanism, according to some embodiments of the present invention.

FIG. 5 shows an exemplary embodiment of an inserter configuration having automatic insertion and retraction capabilities. The inserter (100) includes safety mechanisms for preventing misplacement and inadvertent misfiring. This will be explained further in connection with FIGS. 6 and 7. The inserter also includes a trigger button (330) for actuating a set of springs which fire the penetrating cartridge (150) downward for insertion into the body and for retracting the penetrating member after insertion. The inserter is provided with a housing to accommodate all these mechanisms and elements.

Figure 6:
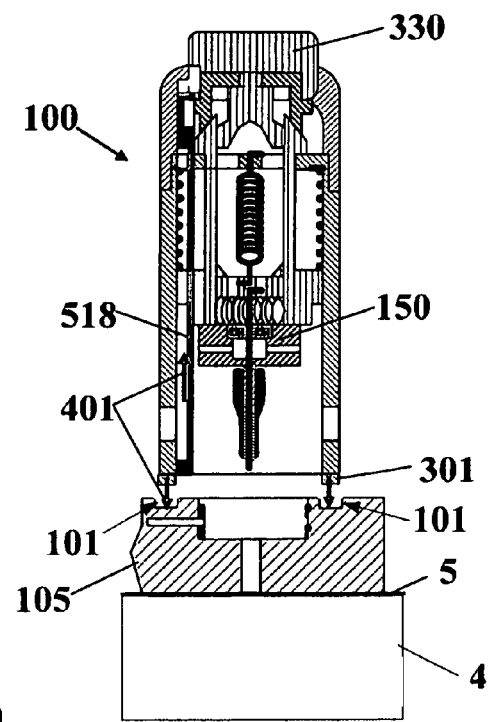
FIG. 6 illustrates an exemplary automatic insertion and retraction mechanism during preparation for firing and further illustrates an exemplary position enabling safety mechanism, according to some embodiments of the present invention.

FIG. 6 illustrates an exemplary embodiment of the automatic inserter (100) and the position enabling safety mechanism (401). An exemplary embodiment of the misfiring safety mechanism (402) is shown in FIG. 7.

The position enabling safety mechanism (401), according to some embodiments, is intended for enabling alignment of the inserter (100) with respect to the well and also for preventing misplacement of the inserter on the patch (105). The position enabling safety mechanism (401) includes indentation grooves (101), located on the upper part of the patch (105), and matching positioning protrusions (301), provided at the lower side of the inserter housing. When placing the inserter (100) on the patch (105), the positioning protrusions (301) are positioned inside the corresponding indentation grooves (101), on the patch (105). Correct positioning of the positioning protrusions (301) inside the indentation grooves (101), allows the movement of a positioning safety rod (518) in an upward direction, thereby by releasing the trigger and thus allowing the firing. When the inserter (100) and the positioning protrusions (301) are not properly located on the patch (105), the positioning safety rod (518) is locked in a safety position, in which it prevents release of the trigger and thus prevents actuating of the inserter.

Figure 7:
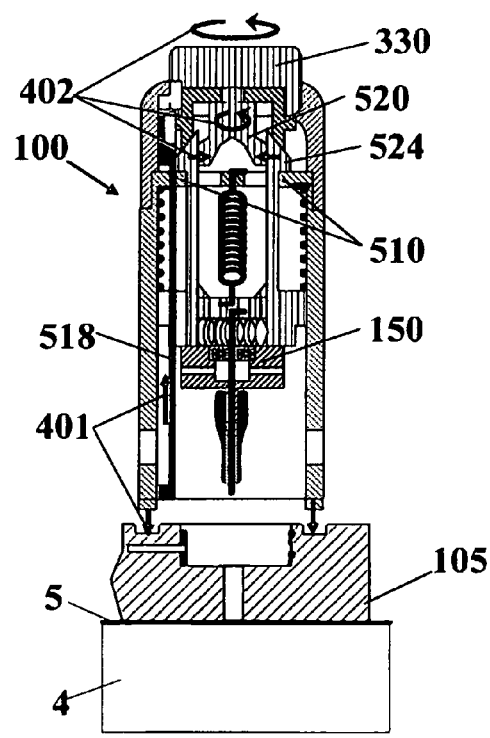
FIG. 7 illustrates an exemplary automatic insertion and retraction mechanism during preparation for firing and further illustrates misfiring of the safety mechanism, according to some embodiments of the present invention.

FIG. 7 illustrates an exemplary embodiment of the inserter (100) with the misfiring safety mechanism (402), intended for preventing inadvertent actuation of the trigger button (330), according to some embodiments of the present invention. The user turns the trigger button (330) of the firing safety mechanism (402) approximately one quarter of a turn (e.g., 90° or thereabout) to release it from the locked position before the trigger button can be pressed for firing. The turning of the trigger button (330) is associated with the rotation of a 2-wing butterfly stopper (520) approximately one quarter of a turn (e.g., 90° or thereabout) in the same direction, for example.

In its initial position, before it has been turned by one quarter of a turn, the 2-wing butterfly stopper (520) holds a pair of springy latch upper protrusions (524) provided at two protruding shoulders (510), preventing any accidental pressing of the trigger button (330). The turn of the 2-wing butterfly stopper (520) by one quarter of a turn, for example, releases the springy latch upper protrusions (524), allowing for later release of the springy latch upper protrusions (524) off these two protruding shoulders (510).

If the user attempts to press the trigger button (330) without first turning the butterfly stopper (520) a specified turning angle (e.g., a quarter of a turn), the 2-wing butterfly stopper (520) holds the springy latch upper protrusions (524) on the protruding shoulders (510) and this prevents the trigger button (330) from being pressed.

The misfiring safety mechanism (402) cannot be used before the positioning safety mechanism (401) has been disabled. The turning of the trigger button (330) can be possible after the positioning safety mechanism (401) has been disabled by proper placement of the inserter (100) on the patch (105). In its safety position, before position enabling, the positioning safety rod (518) is configured to prevent the turn of the 2-wing butterfly stopper (520), thus, preventing the turn of the trigger button (330).

Prevention of accidental turning or pressing of the trigger button (330) is ensured by means of the positioning safety rod (518), which prevents the trigger button (330) from being turned, and by means of the 2-wing butterfly stopper (520), which prevents the trigger button (330) from being pressed.

Figure 8A:
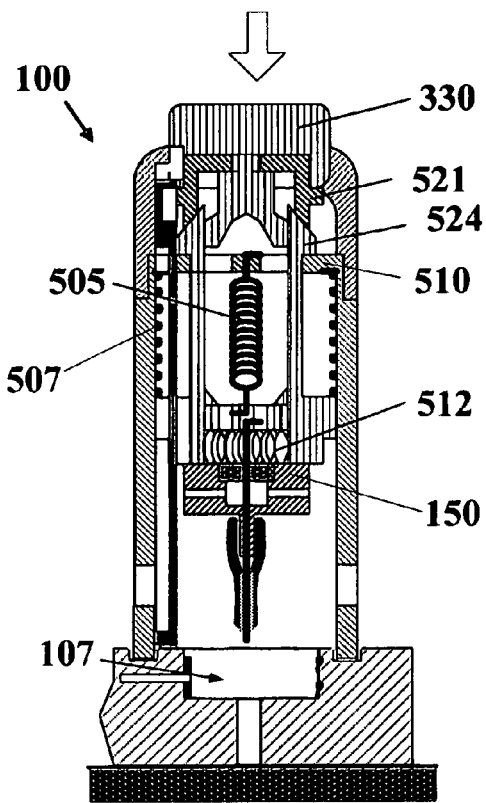
FIGS. 8a-b illustrate an exemplary automatic insertion and retraction mechanism during firing and automatic insertion, according to some embodiments of the present invention.
Figure 8B:
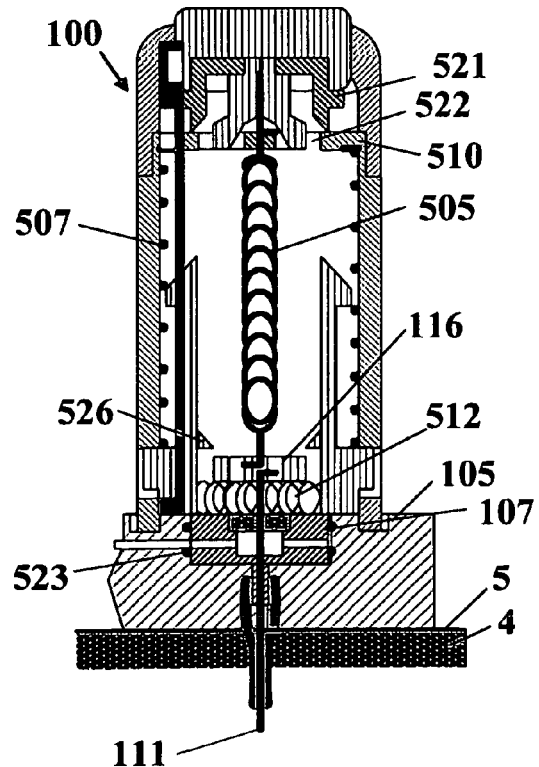

In some embodiments, the trigger button (330) may be fired after all safety mechanisms have been disabled. Insertion is initiated by the patient by pressing the trigger button (330), as shown in FIGS. 8a-b. In some embodiments, a set of springs enables the automatic insertion of the penetrating cartridge and automatic retraction of the penetrating member. This set includes a main spring (507), a retraction spring (505), and an expansion spring (512), as shown in FIG. 8a. The main spring (507) is initially in a loaded state, and is ready to be fired. This spring allows for automatic insertion.

Accordingly, when the trigger button (330) is pressed, a cup (521) moves along a slope of a pair of springy latch upper protrusions (524), pushing the springy latch upper protrusions (524) inwards, and releasing them off the two protruding shoulders (510). The springy latch upper protrusions (524) are then pushed through a pair of notches (522), causing the loaded main spring (507) to be released and to be shot downwards, as shown in FIG. 8b.

The shooting of the main spring (507) downwards, releases the penetrating cartridge (150) which can be shot downwards. A pair of springy latch intermediate protrusions (526) press on the penetrating cartridge (150), preventing it from shooting down all through its downwards movement. The well-sealing cap (118) of the penetrating cartridge (150) enters the well (107) and is retained by means of "O" rings (523). The penetrating member (111) and the cannula (110) are both shot through the skin (5) and into the body (4), completing the automatic insertion process. At this stage, the retraction spring (505) is fully stretched and is ready for retraction.

FIG. 9 shows the automatic retraction process for some of the embodiments of the present invention. During insertion, when the main spring (507) shoots down, a pair of springy latch lower protrusions (528) is pushed outward by the expansion spring (512) towards a pair of corresponding lower notches (530) provided in the inserter (100). The springy latch protrusions (526) move outward as well, releasing the grip portion (116), thus serving as retraction latches. The lower end of the retraction spring (505) is connected to the grip portion (116) of the penetrating cartridge. The release of the grip portion (116) from the springy latch protrusions (526), automatically releases the retraction spring (505) and causes the loaded retraction spring (505) to shoot upwards. The retraction spring (505) pulls the grip portion (116) upward together with the penetrating member (111), while the well sealing cap (118) remains inside the well and the cannula (110) remains inside the body (4). This completes the automatic retraction process.

As seen in FIG. 10, when the automatic retraction process is completed, the inserter (100) contains the used penetrating member (111) in it. The inserter (100) is removed from the patch (105) and is discarded.

Reusable Automatic Inserter with Manual Retraction

In some embodiments, the inserter is provided with an automatic insertion mechanism and is suitable for manual retraction, with an option to reuse the inserter after insertion. In this embodiment, the user can disable all safety mechanisms and fire the trigger. The firing of the trigger initiates the insertion process of the cannula. The penetrating member may be retracted manually. The inserter may be reused for insertion several times by loading a fresh penetrating cartridge into the inserter.

Figure 11:
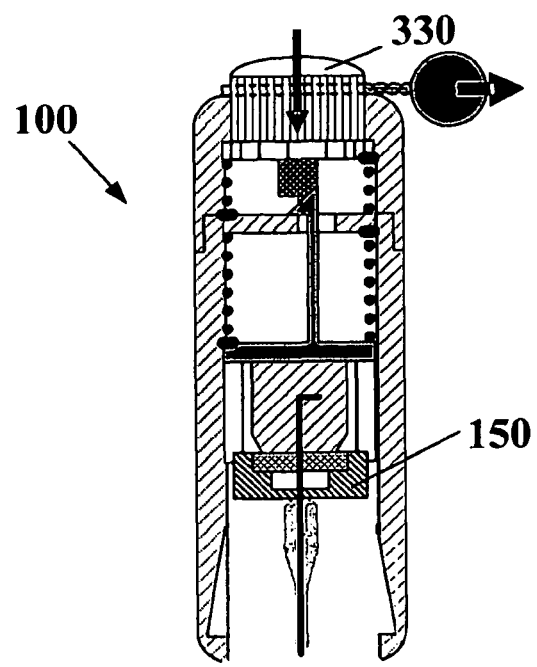
FIG. 11 illustrates an exemplary automatic inserter with manual retraction, according to some embodiments of the present invention.

FIG. 11 illustrates an exemplary inserter that allows automatic insertion and manual retraction. In this embodiment, the inserter (100) can be configured to include substantially the same previously-mentioned safety mechanisms for preventing misplacement and misfiring. The inserter can also include a trigger button (330); a set of springs, which fire the penetrating cartridge (150) in a downward direction for insertion into the body; and a housing to accommodate all the above mechanisms and elements.

Figure 12:
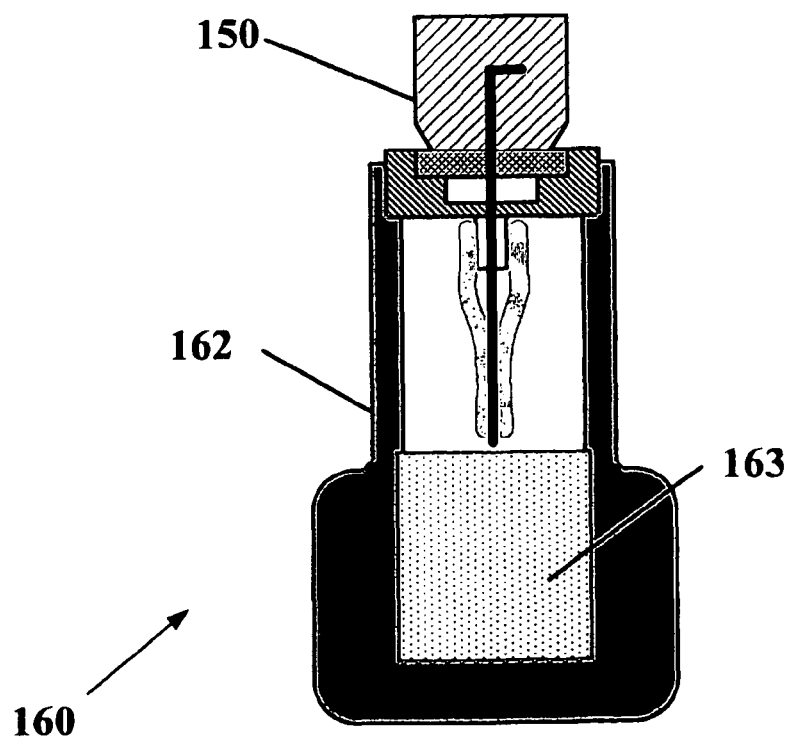
FIG. 12 illustrates an exemplary automatic inserter with manual retraction having a loading kit, according to some embodiments of the present invention.

FIG. 12 illustrates an exemplary loading kit (160), which can be used for reloading a penetrating cartridge (150) into the inserter shown in FIG. 11, according to some embodiments of the present invention. The loading kit (160) includes a loading cup (162), filled with a spongy material (163) that allows holding a penetrating cartridge (150) within the cup.

Figure 13:
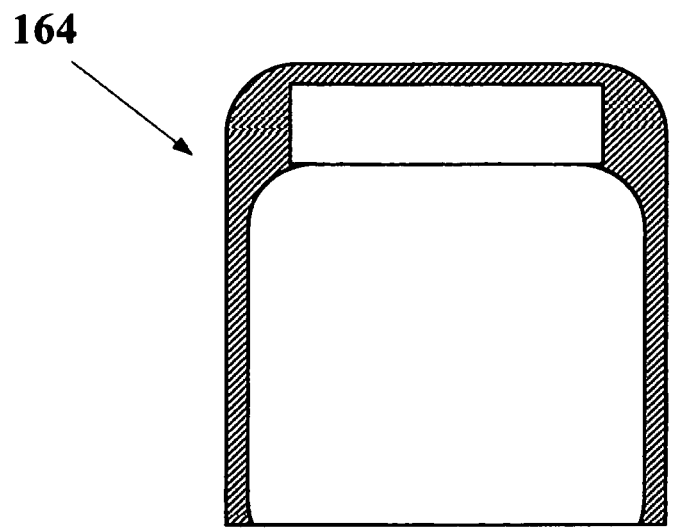
FIG. 13 illustrates an exemplary automatic inserter with manual retraction having a safety cap, according to some embodiments of the present invention.

In some embodiments, the inserter can include a safety cup (164), which fits on top of the inserter, and is removed before the insertion process commences. FIG. 13 illustrates an example of such a safety cup (164) to be fitted on top of the inserter.

In some embodiments, the inserter (100) can include a misfiring safety mechanism (402) for preventing misfiring of the trigger button (330).

Figure 14:
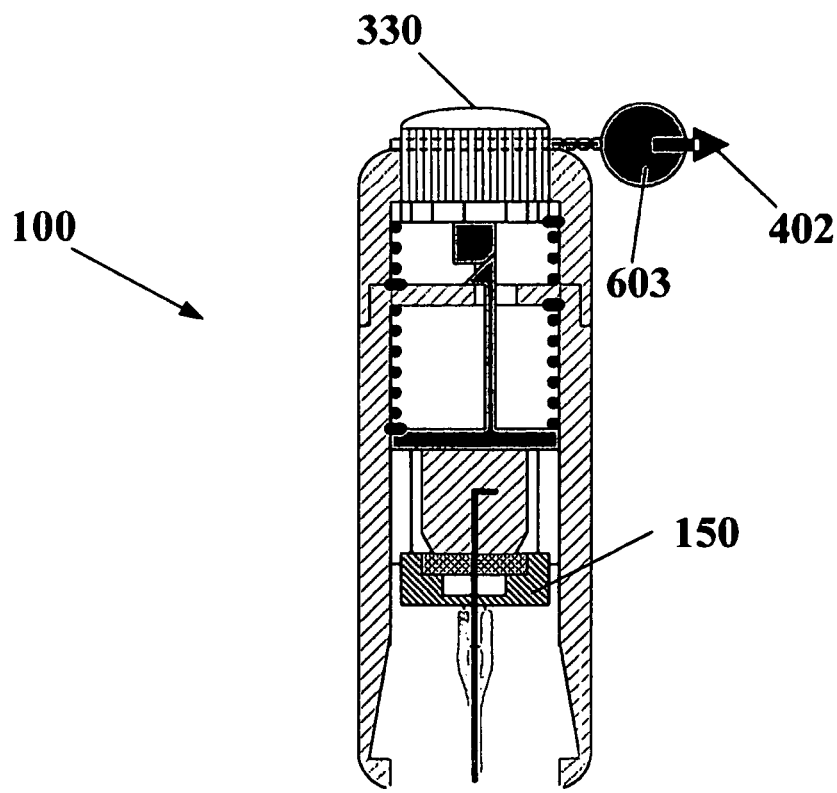
FIG. 14 illustrates an exemplary automatic inserter with manual retraction during preparation for firing and further illustrates misfiring of an exemplary safety mechanism, according to some embodiments of the present invention.

As shown in FIG. 14, the misfiring safety mechanism (402) can be configured to include a safety pin (603) that prevents the trigger button (330) from being pressed, thereby, preventing misfiring of the penetrating cartridge (150). The user can pull the safety pin (603) of the firing safety mechanism (402) outwardly and remove it in order to release the trigger button.

A position safety mechanism can be employed also in this configuration, e.g., by adding positioning protrusions to the base of the inserter. The protrusions are to be inserted into corresponding matching positioning depressions made on the upper part of the patch so as to ensure proper positioning of the inserter on the patch before the insertion process is initiated. The position safety mechanism prevents misplacement of the inserter with respect to the patch, thus, preventing insertion of the penetrating cartridge when it is improperly positioned with respect to the well.

Figure 15A:
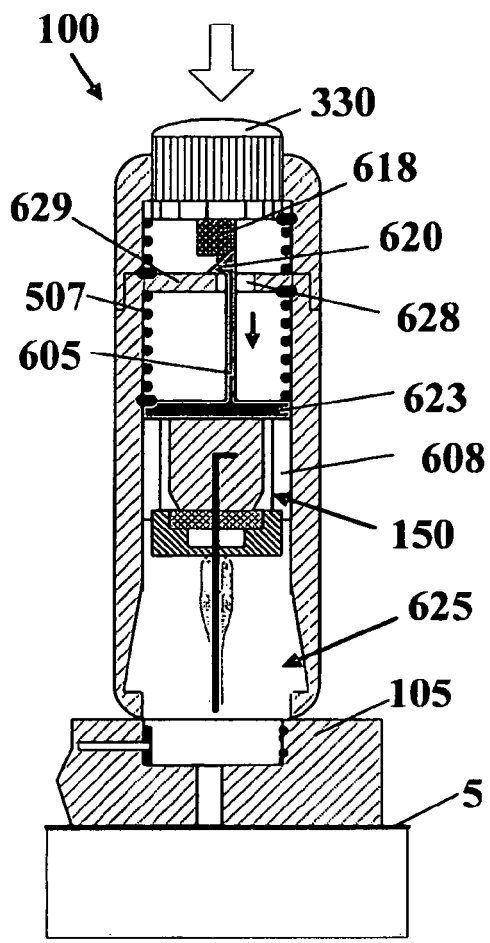
FIGS. 15a-b illustrate an exemplary automatic inserter with manual retraction during firing and automatic insertion, according to some embodiments of the present invention.

In some embodiments, the trigger button (330) can be fired after all safety mechanisms have been disabled. An insertion process can be initiated by the patient by pressing the trigger button (330), as shown in FIGS. 15a-b.

In some embodiments, the inserter includes a main spring (507), a main latch (605), a piston (623), and a set of holding arms (608), enabling the automatic insertion of the penetrating cartridge. The main spring (507) is initially in a loaded state, and is ready to be fired, and it is the spring that allows for automatic insertion.

When the trigger button (330) is pressed, its vertical displacement causes a protrusion (618) to move down and along the slope of the main latch protrusion (620). This causes the main latch protrusion (620) to move aside and down through an opening (628) in a bridge (629) the latch sits on. This in its turn causes the main latch (605) to be released and to move downward, releasing the main spring (507). The main spring (507) is shot downward together with the penetrating cartridge (150) attached to it. This results in the insertion of the penetrating cartridge with the penetrating member through the well provided in the patch (105) and into the skin (5). Throughout its entire movement in a downward direction, the penetrating cartridge (150) is held by a set of holding arms (608), which are connected to the piston (623), as shown in FIG. 15a.

Figure 15B:
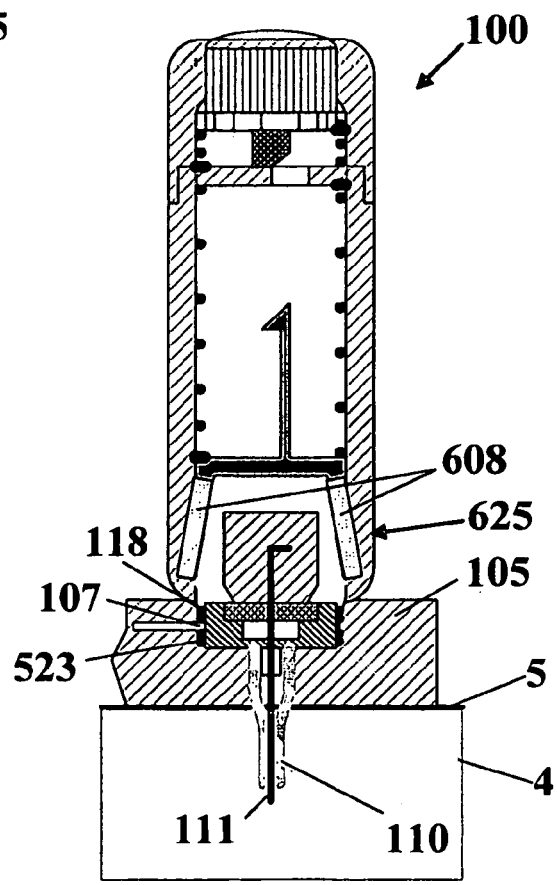

As the penetrating cartridge (150) enters the well provided in the patch (107), the holding arms (608) reach corresponding matching recesses (625) in the inserter (100), and release the grip portion of the penetrating cartridge (150), as shown in FIG. 15b.

The well sealing cap (118) of the penetrating cartridge (150) enters the well (107) provided in the patch (105) and is retained in the well by means of "O" rings (523). One can appreciate that since the sealing cap remains in the well the penetration depth of the penetrating cartridge is limited by the well height.

The penetrating member (111) and the cannula (110) within the penetrating cartridge (150) are both shot through the skin (5) and into the body (4), thereby completing the automatic insertion process.

Figure 16:
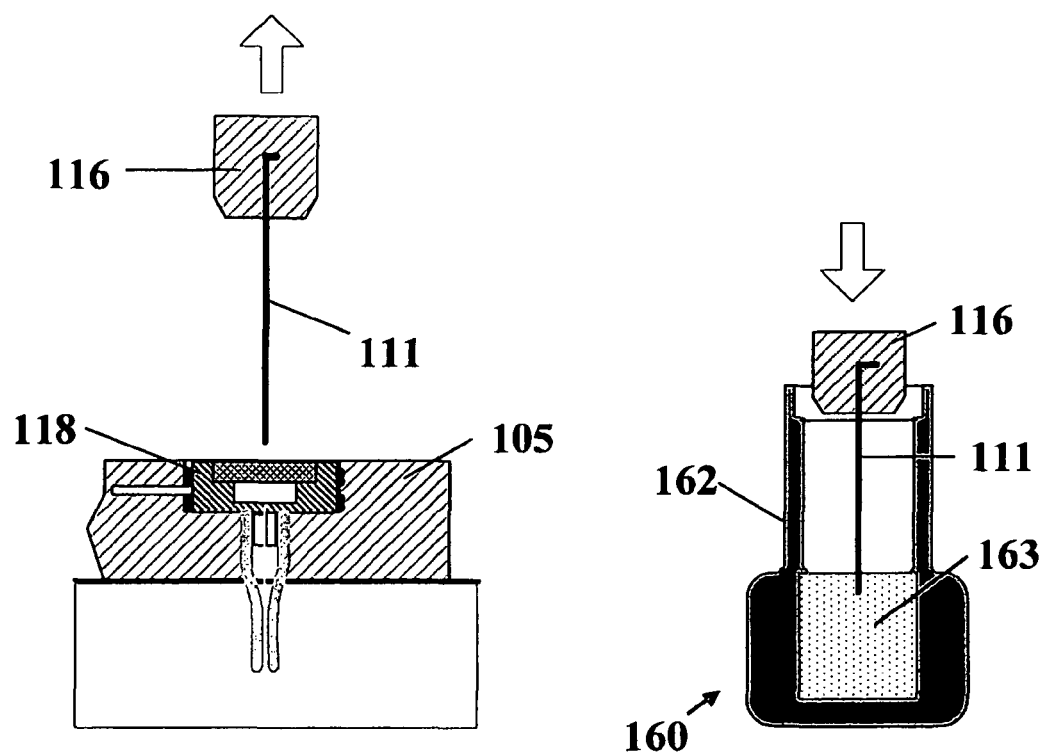
FIG. 16 illustrates an exemplary automatic inserter with manual retraction when insertion complete, according to some embodiments of the present invention.

When the automatic insertion process is completed, the inserter (100) may be moved aside and the penetrating member (111) may be manually removed from the patch (105). To do this, the patient holds the grip portion (116) and pulls it out, along the arrow shown in FIG. 16. The used penetrating member (111) is then stuck in the sponge (163) filling the loading cup (162) within the loading kit (160). The loading kit with the used penetrating cartridge is disposed.

Figure 17A:
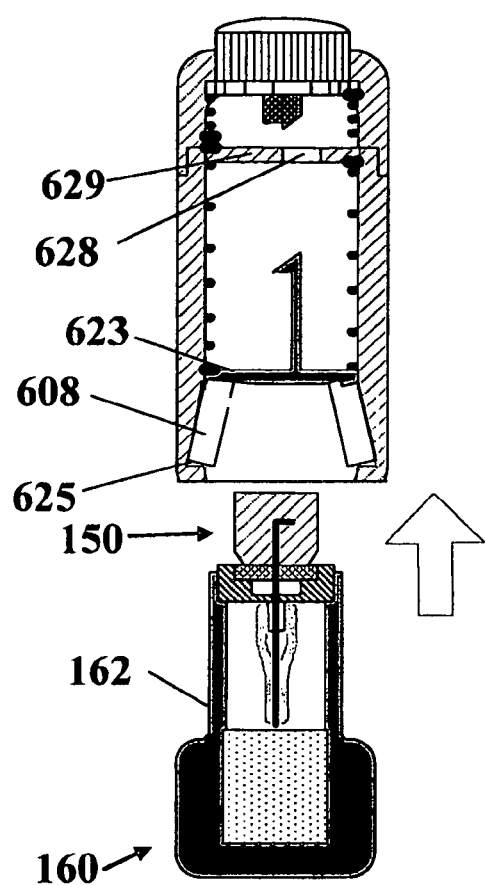
FIGS. 17a-b illustrate an exemplary automatic inserter with manual retraction-during loading, according to some embodiments of the present invention.
Figure 17B:
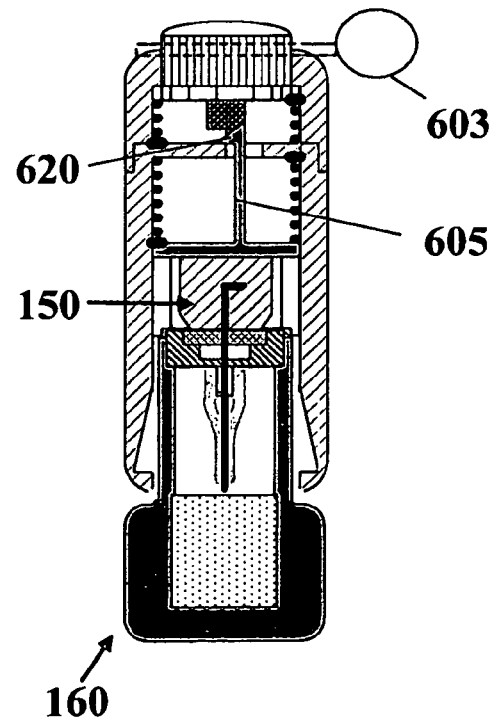

FIGS. 17a-b illustrate exemplary loading of a fresh penetrating cartridge (150) into inserter (100) using a loading kit (160), according to some embodiments of the invention. The loading kit includes a loading cup (162) that holds the fresh penetrating cartridge (150) and guards the penetrating member. The cup is pushed by the patient into the inserter (100) through its bottom opening, so that the upper part of the penetrating cartridge (150) pushes against the piston (623), as shown in FIG. 17a.

The penetrating cartridge (150) pushes the piston (623) in an upward direction, causing the holding arms (608) to leave their corresponding recesses (625) and to grip the penetrating cartridge (150), on its way up. In its upward motion, the penetrating cartridge, which pushes the piston (623), also pushes the main latch (605), until the main latch protrusion (620) is captured by the shoulder (628), as shown in FIG. 17b.

Once latched, a click may be heard, and the loading cup (162) may be pulled out of the inserter (100), and kept for a later use. The loading cup (162) may be used at the end of the insertion process to keep the used penetrating member (111), after its removal from the user's body.

In some embodiments, the patient can insert now the safety pin (603) into a designated place in the trigger button (330), in order to return the misfiring safety mechanism to its enabled state.

In other embodiments, the loading cup (162) cannot be released and pulled out of the inserter (100) until the safety pin (603) is inserted and the misfiring safety mechanism is enabled.

Crank Inserter with Retraction and Loading

In some embodiments, the inserter is provided with a crank mechanism, allowing automatic insertion and automatic refraction, with an option to reuse the inserter after insertion, according to the present invention. In this embodiment, the user disables all safety mechanisms and fires the trigger. The firing of the trigger initiates the insertion of the cannula by the crank mechanism. During one full turn, the crank performs insertion and retraction of the penetrating member, consecutively. The inserter may be reused for insertion several times by reloading a fresh penetrating cartridge into the inserter.

Figure 18A:
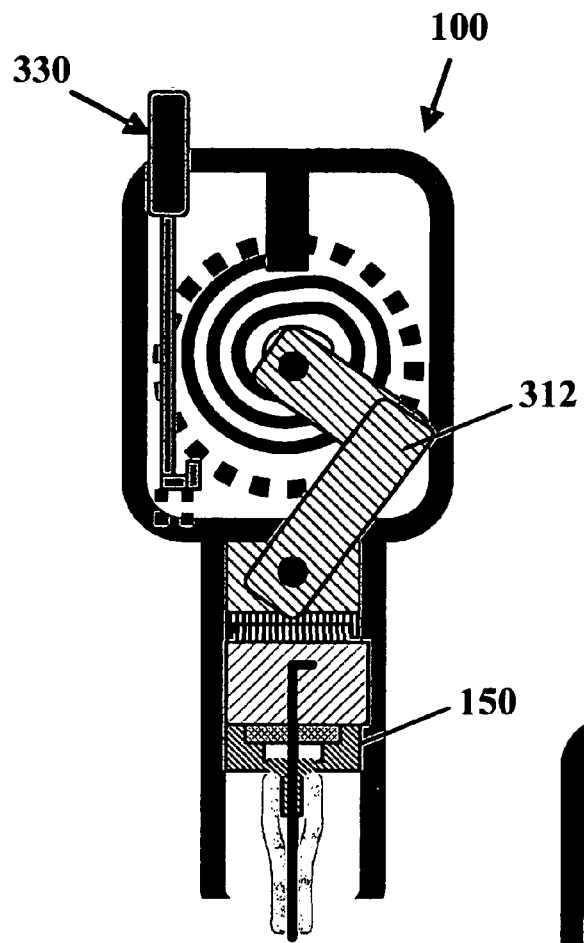
FIGS. 18a-b illustrate an exemplary crank inserter with retraction and loading, according to some embodiments of the present invention.
Figure 18B:
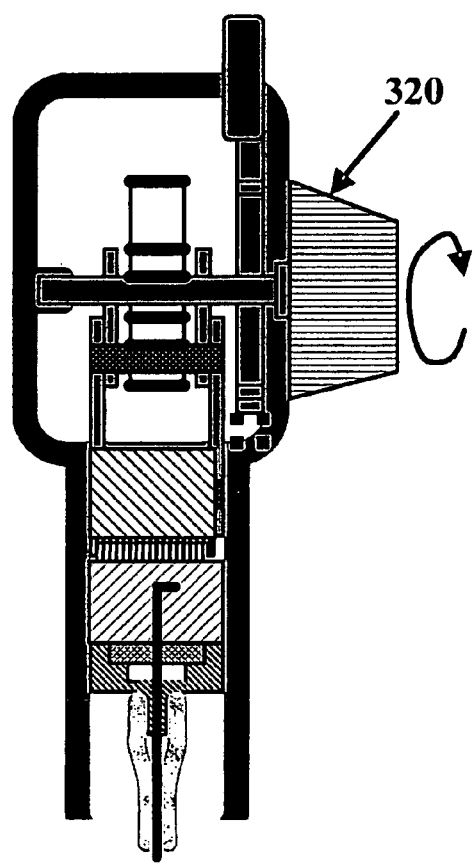

FIGS. 18a-b illustrate an exemplary crank inserter with an automatic insertion and retraction, according to some embodiments of the invention. FIGS. 18a and 18b are two views of the inserter (100). The inserter (100) includes safety mechanisms for preventing misplacement and misfiring; a trigger button (330); a crank mechanism (312), with a cock wheel (320), which while turned causes inserting the penetrating cartridge (150) into the body and retracting the penetrating member after insertion; The inserter comprises also a housing to accommodate the above mechanisms and elements.

Figure 19:
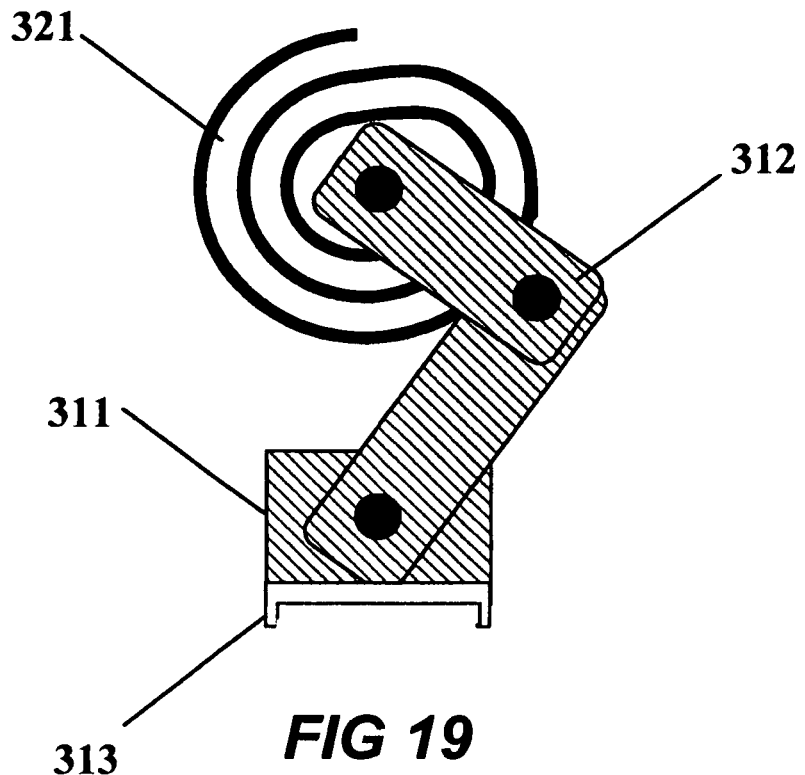
FIG. 19 illustrates an exemplary inserter having a crank, according to some embodiments of the present invention.

In some embodiments, a crank mechanism is used for insertion, as shown in FIG. 19. The crank mechanism includes a spiral spring (321), a crank (312), and a crank piston (311). The end of the crank piston (311) is fitted with the upper connector (313), which connects to the corresponding lower connector (not shown in FIG. 19), provided in the penetrating cartridge.

At its initial position, the spiral spring (321) is not loaded and the crank (312) is in a position, as shown in FIG. 19.

Figure 20:
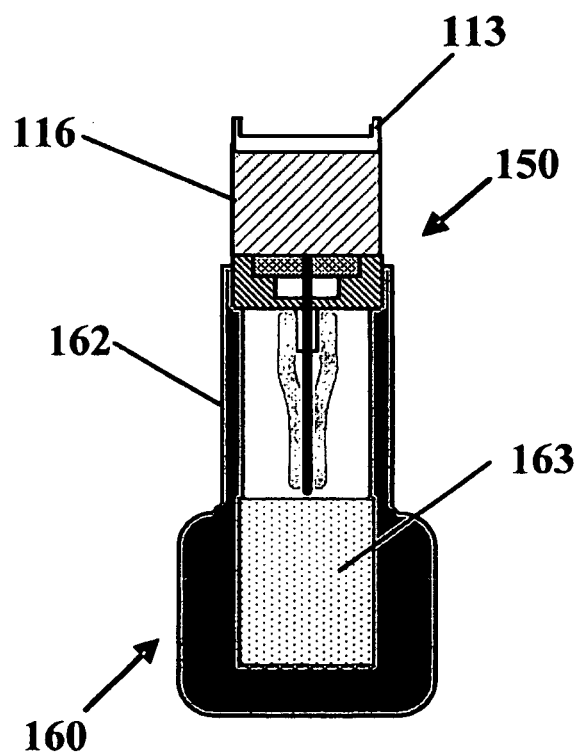
FIG. 20 illustrates an exemplary crank inserter having a penetrating cartridge and loading kit, according to some embodiments of the present invention.

FIG. 20 illustrates the loading kit (160) used for reloading a penetrating cartridge (150) into the crank inserter. In this embodiment, a loading kit (160) can also be provided. The loading kit includes a loading cup (162), filled with spongy material (163) that holds a penetrating cartridge (150). The top part of the penetrating cartridge (150) is fitted with a lower connector (113), which connects to the corresponding upper connector (not shown in FIG. 20), provided inside the inserter (100). The connectors can be any suitable connectors known in the art, e.g. bayonet connectors.

For insertion, the user can load a fresh penetrating cartridge (150) into the inserter (100). The fresh cartridge before loading into inserter is stored in the loading kit (160).

Figure 21A:
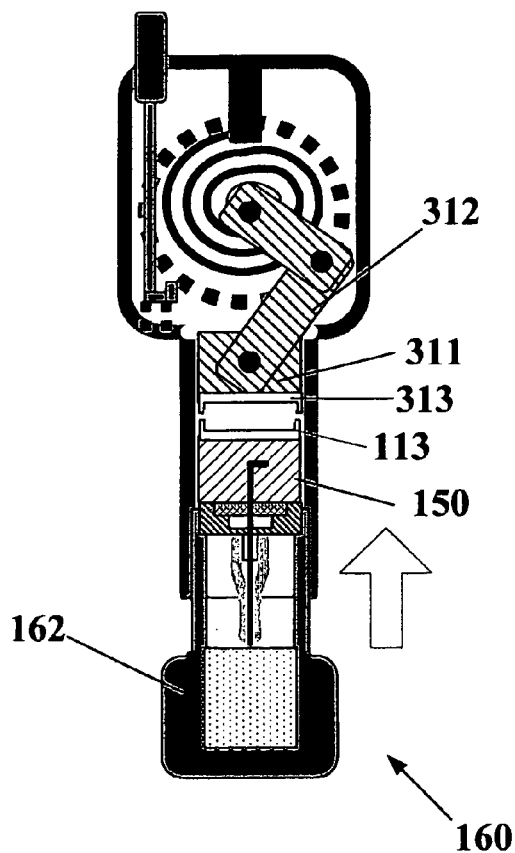
FIGS. 21a-b illustrate an exemplary crank inserter during loading, according to some embodiments of the present invention.
Figure 21B:
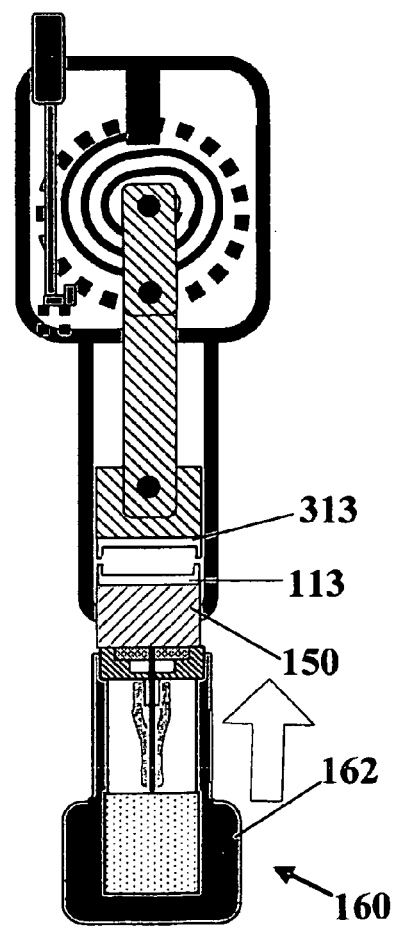

In some embodiments, there are two possible configurations for loading the penetrating cartridge (150): in one embodiment, the crank (312) is in its initial position (as seen in FIG. 21a); in another embodiment, the crank (312) is in an extended position (as seen in FIG. 21b).

In both configurations, the loading cup (162) can be pushed by the user into the inserter (100) through its bottom open portion, so that the upper part of the penetrating cartridge (150) pushes against the crank piston (311). This causes the lower connector (113), provided on the top of the penetrating cartridge (150), to affix to the upper connector (113), provided at the tip of the crank piston (311), resulting in the connection of the two connectors, their latching together. This is shown in FIGS. 21a and 21b.

Once latched, i.e. once the penetrating cartridge (150) is connected to the crank piston (311), the loading cup (162) may be pulled out of the inserter (100), by the user, and kept for the later use. The loading cup (162) may be used at the end of the insertion process to hold the used penetrating member (111), after insertion to the user's body has been completed.

The loading of a fresh penetrating cartridge serves as a safety precaution in the crank inserter.

In some embodiments, the crank inserter (100) includes a misfiring safety mechanism (402) for preventing misfiring of the trigger button (330). The misfiring safety mechanism (402) is shown in FIGS. 22a-b.

The misfiring safety mechanism (402), according to some embodiments of the present invention, includes a cock wheel (320) that can be turned to load a spiral spring (321) and configured to enable the firing. After a fresh penetrating cartridge has been loaded into the inserter, the connector (333) is latched. At this point, the misfiring safety mechanism is held by loading the spiral spring (321). In its initial position, the spiral spring (321) positioned in the inserter is not loaded. Pushing the trigger button (330) before the turning of the cock wheel (320) and loading of the spiral spring (321), prevents firing and thus occasional insertion of the penetrating cartridge (150). The turn of the cock wheel (320) loads the spiral spring (321), which enables firing.

The user turns the cock wheel (320), which loads the spiral spring (321) against a sprocket wheel (322) latched with a ratchet latch (323), which prevents the release of the spiral spring (321), while it is being loaded, and this prevents accidental firing.

Figure 22A:
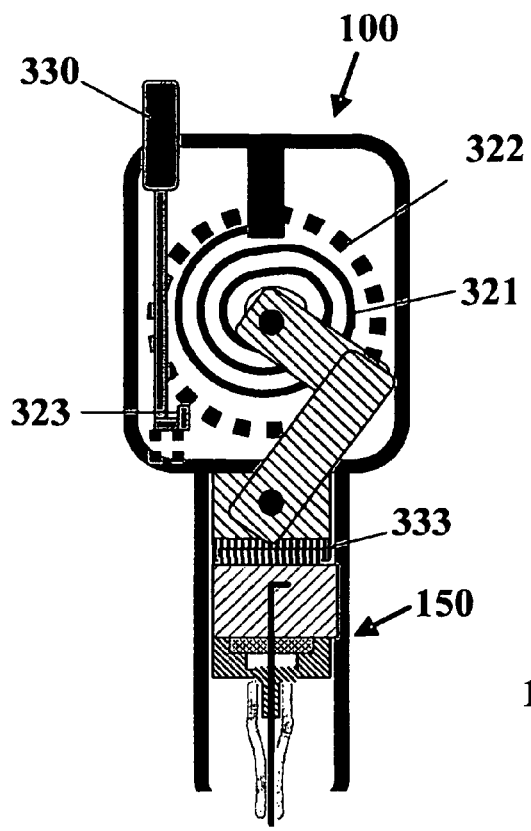
FIGS. 22a-b illustrate an exemplary crank inserter during preparation for firing and further illustrates misfiring of a safety mechanism, according to some embodiments of the present invention.
Figure 22B:
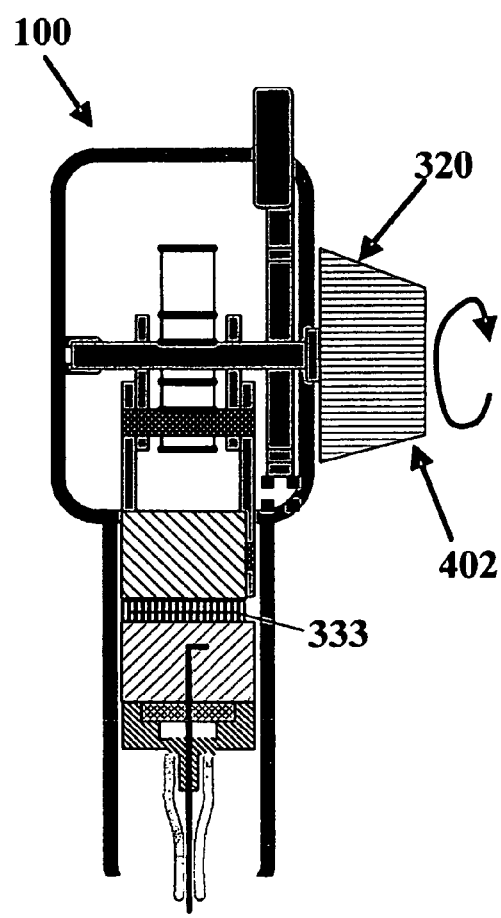

FIGS. 22a-b illustrate a front view (FIG. 22a) and a side view (FIG. 22b) of the crank inserter (100), with a loaded spiral spring (321) according to some embodiments. Loading the spiral spring (321) places the inserter in a "ready to fire" mode, after which insertion process can commence. A position safety mechanism can be added to this embodiment as it has been disclosed in connection with the previous embodiment of the inserter.

Figure 23A:
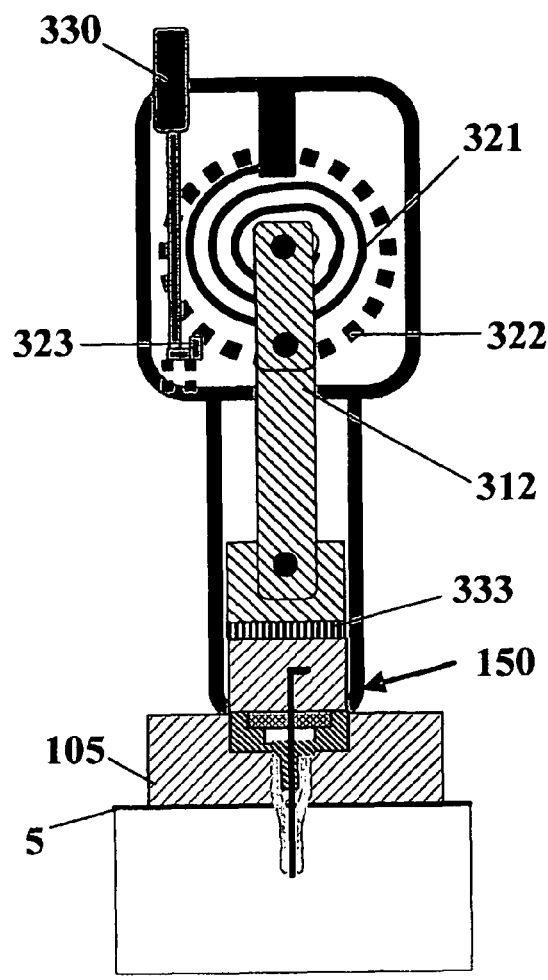
FIGS. 23a-b illustrate an exemplary crank inserter during firing, automatic insertion and retraction, according to some embodiments of the present invention.
Figure 23B:
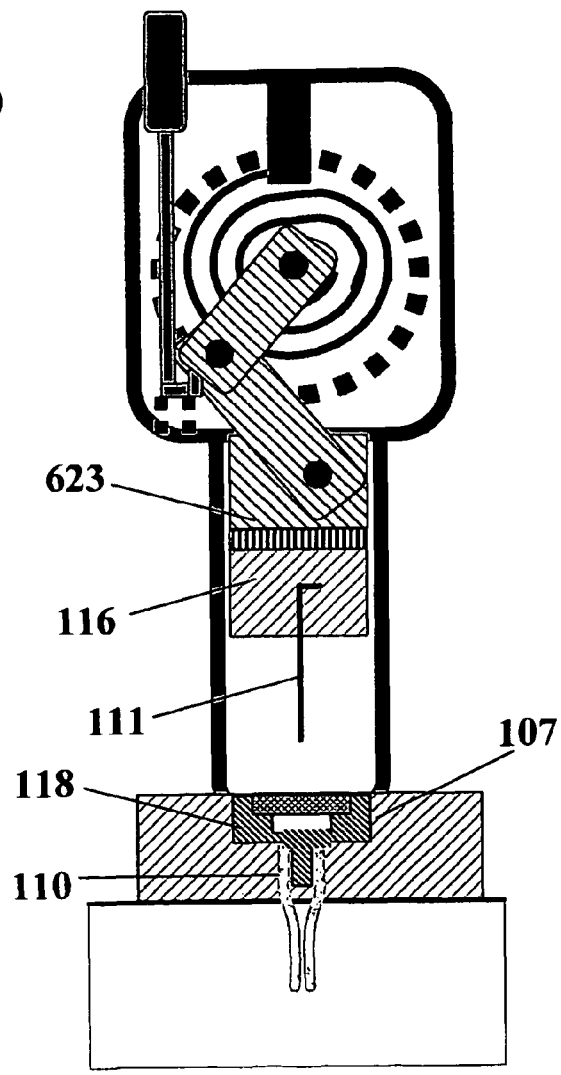

In some embodiments, the trigger button (330) of the crank inserter (100) may be fired only after all safety mechanisms have been disabled. The insertion process is initiated by the patient, by placement of the crank inserter (100) on the patch (105), when the inserter is in "ready to fire" mode. The insertion process is shown in FIGS. 23a-b.

For insertion, the patient presses the trigger button (330), which releases the ratchet latch (323) from the sprocket wheel (322), thus releasing the spiral spring (321). The release of the spiral spring (321) enables the crank (312) to extend, and to push the crank piston (311) vertically downwards. The vertical movement of the crank piston (311), which is attached to the upper part of the penetrating cartridge (150) via bayonet connectors (333), pushes the penetrating cartridge (150) downwards, thus allowing for insertion through the patch (105) and into the skin (5). This is shown in FIG. 23a.

As the penetrating cartridge (150) enters the well (107) in the patch (105), it is retained by means of "O" rings (not shown) in the well (107). The spiral spring (321) has enough potential energy to continue the movement of the crank (312) and to retract the penetrating member (111). The continued movement of the crank (312) pulls the crank piston (311) vertically upwards, thus pulling the grip part (116) and penetrating member (111) upwards and out, while leaving the cannula (110) inside the user's body. This completes the retraction process. This is shown in FIG. 23b.

Figure 24:
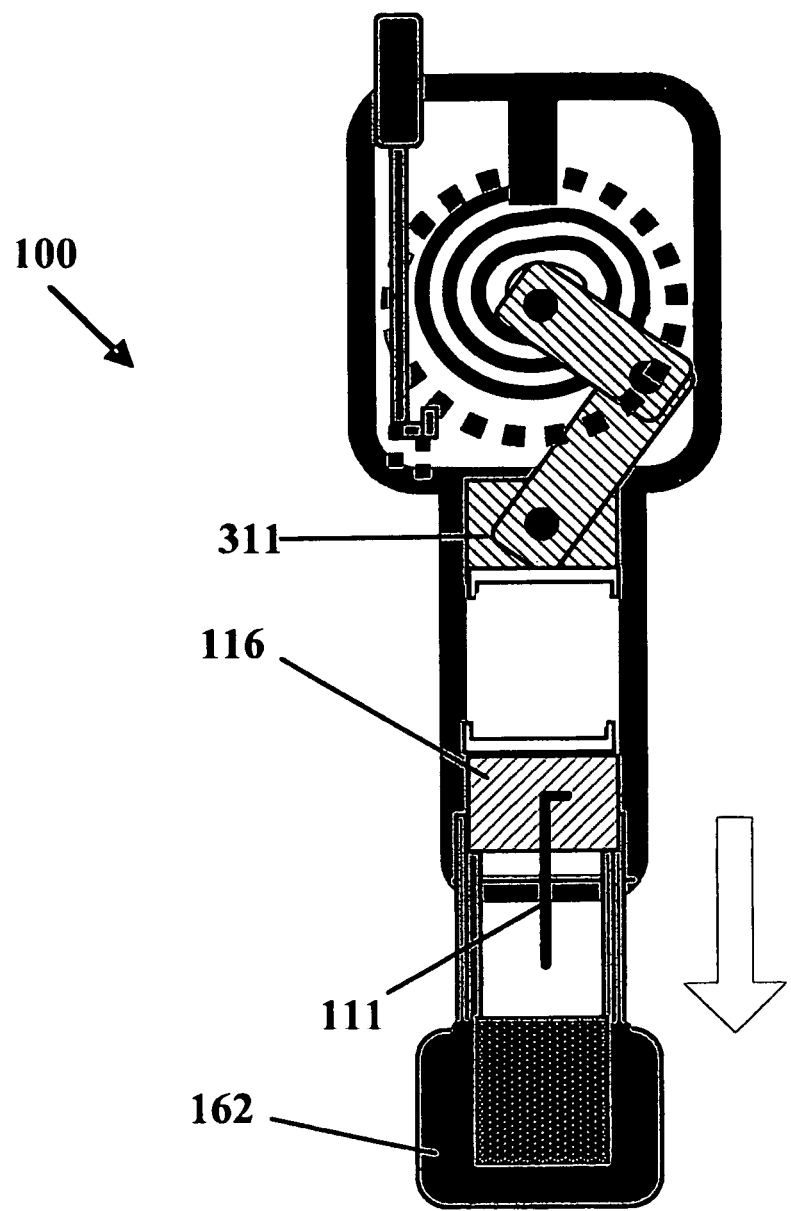
FIG. 24 illustrates an exemplary crank inserter during unloading of the penetrating member, according to some embodiments of the present invention.

Once the penetrating member (111) has been retracted, the inserter (100) is moved aside and away from the patch. Then, the needle cup (162) is attached to the inserter (100). The used penetrating member (111) is detached from the crank piston (311) by pushing the grip portion (116) downward and is then discarded. FIG. 24 shows the unloading of the penetrating member (111) from the inserter (100).

Multiple-needle Inserter

In some embodiments, the inserter can include a drum that is filled with several penetrating cartridges suitable for automatic insertion. In this embodiment, the user disables all safety mechanisms and fires the trigger button. The firing of the trigger button initiates the insertion of the cannula. Upon inserting the user turns the drum for firing the next fresh penetrating cartridge, without a need for reloading the drum. When all cartridges have been fired the drum is replenished with a plurality of fresh cartridges.

Figure 25:
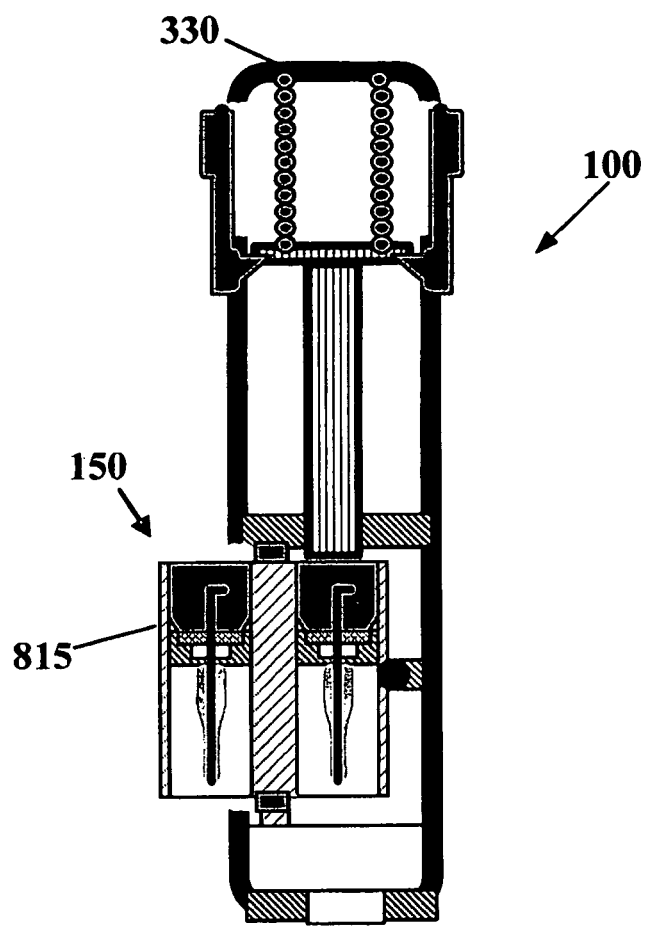
FIG. 25 illustrates an exemplary automatic insertion having a multiple needle inserter, according to some embodiments of the present invention.

In some embodiments, as shown in FIG. 25, a multiple-needle inserter (100) automatically inserts penetrating cartridge (150) into the body. The cartridges are taken from drum (815) preloaded with a plurality of penetrating cartridges (for example 6 cartridges). Retraction of the penetrating member is performed manually.

Figure 26:
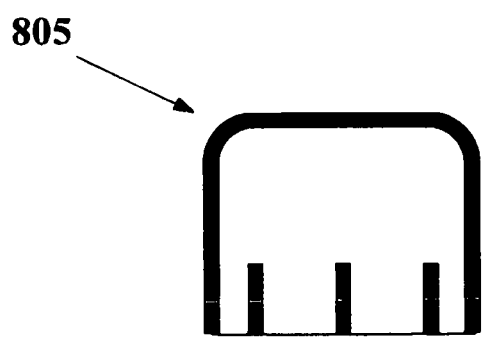
FIG. 26 illustrates an exemplary multiple needles inserter having a safety cup, according to some embodiments of the present invention.

In some embodiments, the inserter can be provided with a protective safety cup (805) which fits on top of the inserter, and is removed before insertion can commence. This protective safety cup (805) prevents accidental misfiring. FIG. 26 illustrates an exemplary safety cup that can be fitted on top of the inserter.

Figure 27:
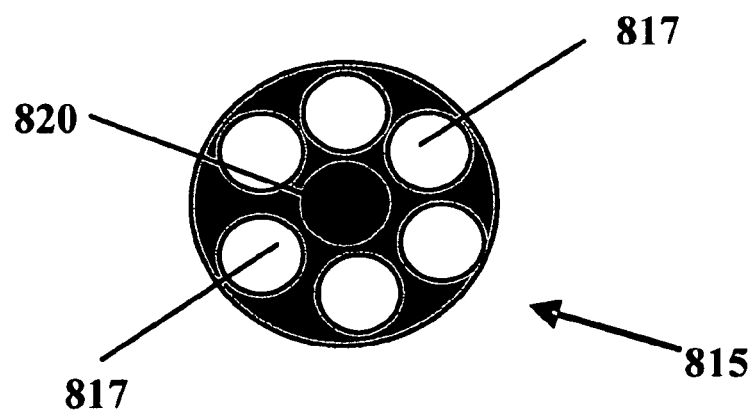
FIG. 27 illustrates an exemplary multiple needles inserter having a needle drum, according to some embodiments of the present invention.

In some embodiments, the cartridge drum (815) includes a revolving needle drum (820) and a plurality of cartridge receiving chambers (817) provided in the drum and situated coaxially with its longitudinal axis (820). The penetrating cartridges can be stored in the receiving chambers (817). FIG. 27 illustrates an exemplary revolving needle drum.

Figure 28:
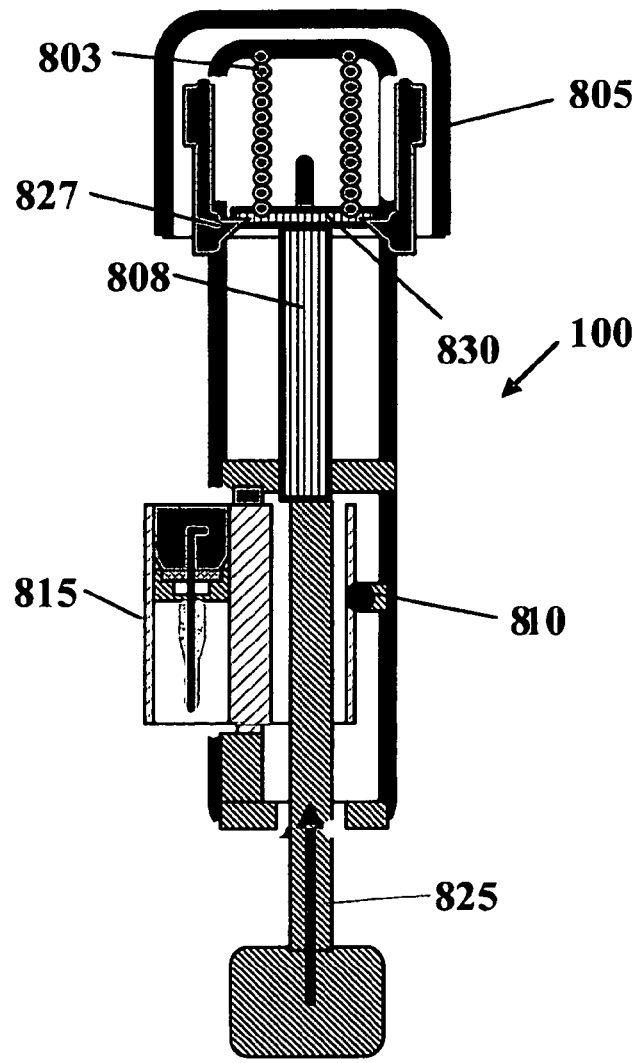
FIG. 28 illustrates an exemplary multiple needles inserter during preparation for firing, according to some embodiments of the present invention.

In some embodiments, the inserter (100) includes a main spring (803) and a reloading rod (825), as shown in FIG. 28. For preparation of the inserter (100) for insertion, the user loads the main spring (803) using the reloading rod (825). The reloading rod (825) pushes a ram rod (808), provided in the inserter, upward until a ram rod latch (830) is captured by trigger protrusions (827). The user then turns the cartridge drum (815) so as to align the loaded chamber with the longitudinal axis of the inserter, until the cartridge drum (815) is captured by an indexing ball (810) and a "click" is heard. For firing, the user removes the protective safety cup (805), which prevents accidental firing. After completing these steps, the inserter (100) is in a "ready to fire" mode.

Figure 29A:
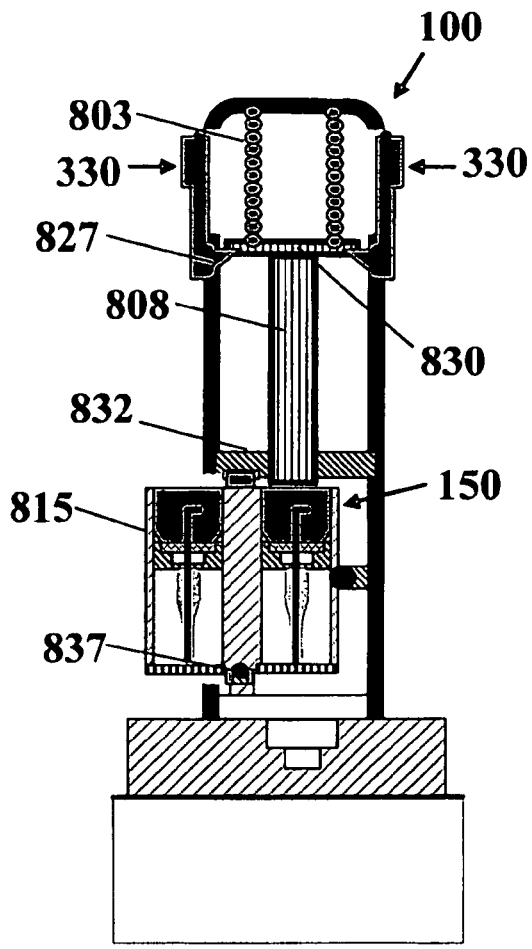
FIGS. 29a-b illustrate an exemplary multiple needles inserter during firing and insertion, according to some embodiments of the present invention.
Figure 29B:
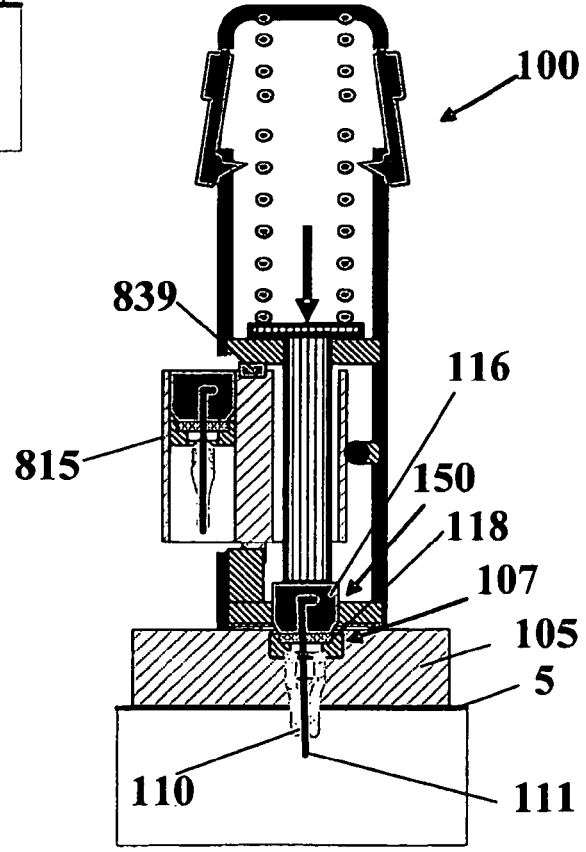

FIGS. 29a-b illustrate exemplary firing and insertion procedures. For insertion procedure, the user presses the trigger by simultaneously pressing two lateral trigger buttons (330). This releases the ram rod latch (830) from the trigger protrusions (827). This, in turn, releases the main spring (803), which fires downward with the ram rod latch (830), which is in turn stopped by the bracket (832), as shown in FIGS. 29a and 29b.

As shown in FIG. 29b, the penetrating cartridge (150) penetrates the patch (105) and enters the well (107) in the patch (105). The well sealing cap (118) within the penetrating cartridge (150) is retained by means of "O" rings (not shown) in the well (107); the penetrating member (111) with cannula (110) penetrate the user's skin (5). The penetrating member (111) may be manually retracted from the body by holding its grip part (116) and is then disposed of. At the end of the insertion process, the user places the protective safety cap on the inserter (100) to cover the trigger buttons, to prevent them from being unintentionally pressed. When the cartridge drum (815) is empty, it may be removed by pulling it out from a clamp (839) and disengaging it from the spring ball (837). To reload a new cartridge drum (815), the user removes it from its package, places it at the lower part of the inserter (100) on the spring ball (837) and pushes the clamp (839) inwards.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

What is claimed is:

1. An insertion device for use with a device for delivery of a therapeutic fluid into a body of a patient and/or for sensing of a bodily analyte, the insertion device comprising:
   a housing having accommodated therein: at least one penetrating cartridge provided with a penetrating member and a subcutaneously insertable element;
   a displacement mechanism which upon actuation is capable of protracting said penetrating cartridge towards the device for delivery and/or sensing and inserting the subcutaneously insertable element into a subcutaneous compartment of the body, the displacement mechanism being movable from a first position in which the displacement mechanism is prevented from actuation to a second position in which the displacement mechanism can be actuated; and
   a safety means for allowing the displacement mechanism to move from the first position to the second position for actuation only when the insertion device has been placed in an appropriate position on the device for delivery and/or sensing;
   wherein said insertion device is suitable for inserting the subcutaneously insertable element into the subcutaneous compartment of the body via an opening provided in the device for delivery and/or sensing and said insertion device allows evacuation of the penetrating member from the subcutaneous compartment via the opening.

2. The insertion device as defined in claim 1, wherein the device for delivery and/or for sensing is skin adherable; and said opening is configured as a well.

3. The insertion device as defined in claim 2, wherein said subcutaneously insertable element is a cannula for delivery of the therapeutic fluid.

4. The insertion device as defined in claim 3, wherein the delivery and/or sensing device is fitted with a reservoir for storing the therapeutic fluid and said well provides fluid communication between the cannula and the reservoir.

5. The insertion device as defined in claim 2, wherein said subcutaneously insertable element is a sensor for sensing the bodily analyte.

6. The insertion device as defined in claim 2, wherein said well is pivotable.

7. The insertion device as defined in claim 2, wherein said housing is provided with at least one protrusion; and said device for delivery and/or for sensing is provided with at least one corresponding depression surrounding the well, such that upon insertion of the at least one protrusion into the at least one depression, the penetrating cartridge can be aligned with the well and disable the safety means to allow actuation of the displacement mechanism.

8. The insertion device as defined in claim 2, wherein said penetrating cartridge further comprises a sealing cap, which is receivable in the well upon inserting the penetrating cartridge; and said cap is adapted to seal the well after the penetrating cartridge has been inserted and after the said penetrating member has been evacuated.

9. A method for inserting a subcutaneously insertable element within a subcutaneous compartment of a body of a patient using an insertion device according to claim 8, the method comprising the steps of:

inserting the penetrating member and the subcutaneously insertable element into the subcutaneous compartment via the well; and removing the penetrating member from the subcutaneous compartment while retaining the subcutaneously insertable element in the subcutaneous compartment and while sealing an upper opening of the well.

10. The insertion device as defined in claim 1, wherein said displacement mechanism is manually actuatable.

11. The insertion device as defined in claim 10, further comprising a manually actuatable knob for actuation of the displacement mechanism; wherein the safety means is configured to prevent inadvertent actuation of the knob.

12. The insertion device of claim 11, wherein the safety means includes a safety rod configured to move from a first position in which the knob is locked to a second position to allow actuation of the knob thereby allowing actuation of the displacement mechanism.

13. The insertion device as defined in claim 1, further comprising a retracting means operatively coupled with the penetrating cartridge and capable of automatically retracting the penetrating member from the subcutaneous compartment, while enabling the subcutaneously insertable element to retain within the subcutaneous compartment.

14. The insertion device as defined in claim 13, wherein the penetrating member includes an insertion end for penetrating the subcutaneous tissue; and a grip portion located opposite the insertion end; wherein the grip portion enables the penetrating member to be protracted and retracted.

15. The insertion device as defined in claim 13, wherein the penetrating member is a needle.

16. The insertion device as defined in claim 13, wherein said displacement mechanism is fitted with a coiled spring for protracting the penetrating cartridge; and said retracting means further comprises a coiled spring for retracting the penetrating member.

17. The insertion device as defined in claim 13, wherein said displacement mechanism further comprises a crank actuatable by a cock-wheel.

18. The insertion device as defined in claim 17, further comprising a misfiring safety mechanism.

19. The insertion device as defined in claim 1, wherein said safety means includes a safety rod which enables protracting of the penetrating cartridge only when the penetrating cartridge is aligned with the well.

20. The insertion device of claim 19, wherein the safety rod is configured to move from a first position in which the displacement mechanism is locked to a second position to allow actuation of the displacement mechanism when the penetrating cartridge is aligned with the well.

21. The insertion device as defined in claim 1, wherein the therapeutic fluid is insulin.

22. The insertion device as defined in claim 1, wherein the bodily analyte is glucose.

23. The insertion device as defined in claim 1, wherein the insertion device is reusable.

24. The insertion device as defined in claim 1, wherein the insertion device is disposable.

25. The insertion device as defined in claim 1, further comprising a drum which is preloadable with a plurality of penetrating cartridges; said drum is provided with a plurality of chambers for receiving the plurality of penetrating cartridges and said drum is displaceable with respect to the housing so as to align a chamber with a longitudinal axis of the insertion device and to enable protracting of the penetrating cartridge received in the chamber.

26. The insertion device of claim 1, wherein the insertion device is pivotable with the opening of the device for delivery and/or sensing to insert the subcutaneously insertable element into the body at a penetrating angle.

27. The insertion device according to claim 1, wherein the displacement mechanism comprises a trigger knob rotatable to move from the first position to the second position.

28. A method for delivering a therapeutic fluid to a subcutaneous compartment in a body of a patient and/or for sensing of a bodily analyte, said method comprising the steps of:
providing a device for delivery of the therapeutic fluid and/or for sensing the bodily analyte;
providing an insertion device comprising: at least one penetrating cartridge having a penetrating member and a subcutaneously insertable element; said insertion device further comprising a displacement mechanism and a safety means for allowing the displacement mechanism to actuate only when the insertion device has been placed in an appropriate position on the device and the displacement mechanism has been moved from a first position in which the displacement mechanism is prevented from actuation to a second position in which the displacement mechanism can be actuated;
placing the insertion device on the device for delivery and/or sensing in the appropriate position to disable the safety means;
after the insertion device has been placed on the device for delivery and/or sensing in the appropriate position, moving the displacement mechanism of the insertion device from the first position to the second position;
actuating the displacement mechanism at the second position thereby protracting the penetrating cartridge by the displacement mechanism towards the body of the patient so as to insert the subcutaneously insertable element into the subcutaneous compartment via an opening provided at the device for delivery and/or for sensing;
removing the penetrating member from the subcutaneous compartment while allowing the subcutaneously insertable element to remain in the subcutaneous compartment; and
delivering the therapeutic fluid to the subcutaneous compartment through the subcutaneously insertable element and/or sensing the bodily analyte.

29. The method according to claim 28, wherein the protracting step is performed automatically.

30. The method according to claim 28, wherein the removing step is performed manually.

31. The method according to claim 28, wherein the removing step is performed automatically.

32. The method according to claim 28, wherein said therapeutic fluid is insulin and said subcutaneously insertable element is a cannula.

33. The method according to claim 28, wherein said bodily analyte is glucose and said subcutaneously insertable element is a sensor.

34. The method of claim 28, further comprising pivoting the insertion device with the opening of the device for delivery and/or sensing at an angle with respect to the body of the patient.

35. The method according to claim 28, wherein the moving the displacement mechanism of the insertion device comprises rotating a trigger knob of the displacement mechanism from the first position to the second position.

* * * * *